US006497873B1

(12) United States Patent
Whitt et al.

(10) Patent No.: US 6,497,873 B1
(45) Date of Patent: Dec. 24, 2002

(54) RECOMBINANT RHABDOVIRUS CONTAINING A HETEROLOGOUS FUSION PROTEIN

(75) Inventors: Michael A. Whitt, Cordova, TN (US); Clinton S. Robison, Memphis, TN (US)

(73) Assignee: The University of Tennessee Research Corporation, Knoxville, TN (US)

(*) Notice: Subject to any disclaimer, the term of this patent is extended or adjusted under 35 U.S.C. 154(b) by 0 days.

(21) Appl. No.: 09/217,967

(22) Filed: Dec. 22, 1998

Related U.S. Application Data

(60) Provisional application No. 60/068,472, filed on Dec. 22, 1997.
(51) Int. Cl.[7] .......................... A01N 63/00; C12N 7/00; C12N 7/02; C12N 15/00; C12N 15/63
(52) U.S. Cl. .................. 424/93.2; 435/235.1; 435/239; 435/320.1; 435/440; 435/455
(58) Field of Search ...................... 424/93.2; 435/235.1, 435/320.1, 440, 455, 239

(56) References Cited

PUBLICATIONS

Hale et al. Cytotoxic T Lymphocytes Specific for Vesicular Stomatitis Virus Recognize the Major Surface Glycoprotein of VSV. Antiviral Research, vol. 1, pp. 63–70, 1981.*
Chu, Te–Hua Tearina et al., Toward Highly Efficient Cell–Type–Specific Gene Transfer with Retroviral Vectors Displaying Single–Chain Antibodies, *Journal Of Virology*, vol. 71, No. 1, pp. 720–725, Jan. 1997.
Dolter, Karen E. et al., Incorporation of CD4 into Virions by a Recombinant Herpes Simplex Virus, *Journal of Virology*, vol. 67, No. 1, pp. 189–195, Jan. 1993.
Fuerst, Thomas R. et al., Use of a Hybrid Vaccinia Virus–T7 RNA Polymerase System for Expression of Target Genes, *Molecular and Cellular Biology*, vol. 7, No. 7, pp. 2538–2544, Jul. 1987.
Galmiche, Marie C. et al., Expression of a functional single chain antibody on the surface of extracellular enveloped vaccinia virus as a step towards selective tumour cell targeting, *Journal of General Virology*, vol. 78, pp. 3019–3027, Nov., 1997.
Johnson, J. Erik et al., Specific Targeting to CD4+ Cells of Recombinant Vesicular Stomatitis Viruses Encoding Human Immunodeficiency Virus Envelope Proteins, *Journal of Virology*, vol. 71, No. 7, pp. 5060–5068, Jul. 1997.
Lamb, Robert A., Minireview: Paramyxovirus Fusion: A Hypothesis for Changes, *Virology*, vol. 197, pp. 1–11, 1993.
Marin, Mariana et al., Targeted Infection of Human Cells via Major Histocompatibility Complex Class I Molecules by Moloney Murine Leukemia Virus–Derived Viruses Displaying Single–Chain Antibody Fragment–Envelope Fusion Proteins, *Journal of Virology*, vol. 70, No. 5, pp. 2957–2962, May 1996.

Mebatsion, Teshome et al., Binding of Rabies Virus Particles in the Absence of the Spike Glycoprotein, *Cell*, vol. 84, pp. 941–951, Mar. 22, 1996.
Mebatsion, Teshome et al., A CXCR4/CD4 Pseudotype Rhabdovirus That Selectively Infects HIV–1 Envelope Protein–Expressing Cells, *Cell*, vol. 90, pp 841–847, Sep. 5, 1997.
Mebatsion, Teshome et al., Specific infection of CD4+ target cells recombinant rabies virus pseudotypes carrying the HIV–1 envelope spike protein, *Proc. Natl. Acad. Sci.. USA*, vol. 93, pp. 11366–11370, Oct. 1996.
Nolan, Garry P., Harnessing Viral Devices as Pharmaceuticals: Fighting HIV–1's Fire with Fire, *Cell*, vol. 90, pp. 821–824, Sep. 5, 1997.
Pattnaik, Asit K. et al., Cells that express all five proteins of vesicular stomatitis virus from cloned cDNAs support replication, assembly, and budding of defective interfering particles, *Proc. Natl. Acad. Sci. USA*, vol. 88, pp. 1379–1383, Feb. 1991.
Pattnaik, Asit K. et al., Infectious Defective Interfering Particles of VSV from Transcripts of a cDNA Clone, *Cell*, vol.69, pp. 1011–1020, Jun. 12, 1992.
Pattnaik, Asit K. et al., Replication and Amplification of Defective Interfering Particle RNAs of Vesicular Stomatitis Virus in Cells Expressing Viral Proteins from Vectors Containing Cloned cDNAs, *Journal of Virology*, vol. 64, No. 6, pp. 2948–2957, Jun. 1990.
Schnell, Matthias J. et al., Foreign glycoproteins expressed from recombinant vesicular stomatitis viruses are incorporated efficiently into virus particles, *Proc. Natl. Acad. Sci.. USA*, vol. 93, pp. 11359–11365, Oct. 1996.
Schnell, Matthias J. et al., Infectious rabies viruses from cloned cDNA., *The EMBO Journal*, vol. 13, No. 18, pp. 4195–4203, 1994.
Schnell, Matthias J. et al., Construction of a Novel Virus That Targets HIV–1 Infected Cells and Controls HIV–1 Infection, *Cell*, vol. 90, pp. 849–857, Sep. 5, 1997.
Stillman, Elizabeth A. et al., Replication and Amplification of Novel Vesicular Stomatitis Virus Minigenomes Encoding Viral Structural Proteins, *Journal of Virology*, vol. 69, No. 5, pp. 2946–2953, May 1995.

(List continued on next page.)

*Primary Examiner*—Deborah J. Reynolds
*Assistant Examiner*—Shin-Lin Chen
(74) *Attorney, Agent, or Firm*—Mark S. Cohen; Eitan, Pearl, Latzer & Cohen-Zedek

(57) ABSTRACT

This invention relates to a composition comprising a recombinant or genetically engineered Rhabdovirus that expresses a Fusion Protein, such as the F protein of the Paramyxovirus SV5 strain. This recombinant Rhabdovirus may express other non-Rhabdovirus attachment proteins and/or an enhancer protein. The invention also relates to methods of making recombinant Rhabdoviruses which express an F Protein. These recombinant compositions can be used for purposes of research, as well as for diagnostic and therapeutic compositions for treatment of diseases.

28 Claims, 10 Drawing Sheets

PUBLICATIONS

Figure 1A:
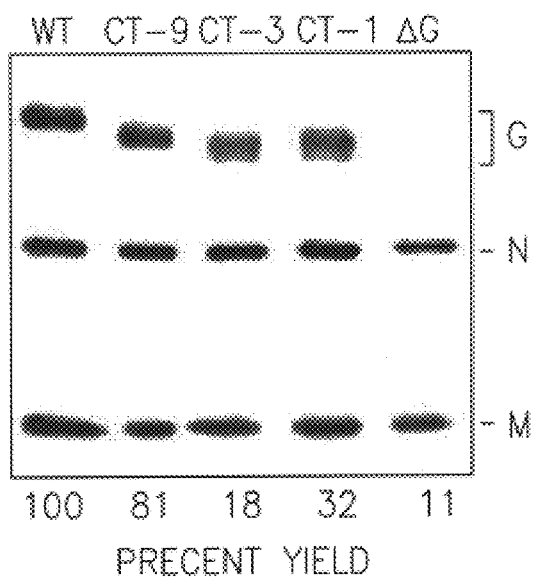
Figure 1B:
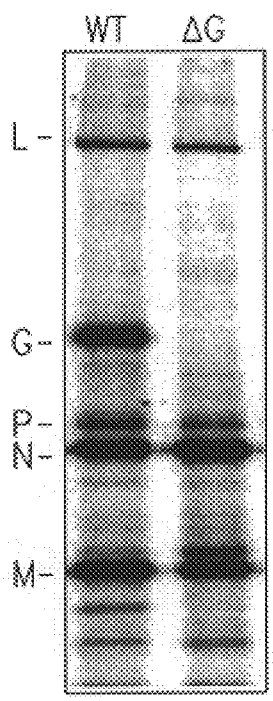

Takada, Ayato et al., A System for functional analysis of Ebola virus glycoprotein, *Proc. Natl Acad. Sci., USA*, vol. 94, pp. 14764–14769, Dec. 1997.

Wertz, Gail W. et al., Extent of terminal complementarity modulates the balance between transcription and replication of vesicular stomatitis virus RNA, *Proc. Natl. Acad. Sci., USA*, vol. 91, pp. 8587–8591, Aug. 1994.

Whelan, Sean P.J. et al., Efficiency recovery of infectious vesicular stomatitis virus entirely from cDNA clones, *Proc. Natl. Acad. Sci., USA*, vol. 92, pp. 8388–8392, Aug. 1995.

Young, John A. T. et al., Efficient Incorporation of Human CD4 Protein into Avian Leukosis Virus Particles, *Science*, vol. 250, pp. 1421–1423, Dec. 7, 1990.

* cited by examiner

FIG.4

ANTI-VSA N PROTEIN    PHASE CONTRAST

VSV/CD4-G

VSV/CD4-Q427

VSV/HAGS/CD4-G

SEQUENCE LISTING

<160> NUMBER OF SEQ ID NOS: 3

<210> SEQ ID NO 1
<211> LENGTH: 511
<212> TYPE: PRT
<213> ORGANISM: Rhabdovirus

<400> SEQUENCE: 1

```
Met Lys Cys Phe Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Gly Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
```

```
              130                 135                 140
Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
                195                 200                 205

Arg Glu Leu Ser Ser Leu Gly Lys Glu Gly Thr Gly Phe Arg Ser Asn
            210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Gly Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Ile Leu Phe Gly Asp Thr Gly Leu Ser Lys
            435                 440                 445

Asn Pro Ile Asp Phe Val Glu Gly Trp Phe Ser Trp Lys Ser Ser
            450                 455                 460

Ile Ala Ser Phe Phe Ile Ile Gly Leu Ile Gly Leu Phe Leu
465                 470                 475                 480

Val Leu Arg Val Gly Ile Tyr Leu Tyr Ile Lys Leu Lys His Thr Lys
                485                 490                 495

Lys Arg Gln Ile Tyr Thr Asp Ile Glu Met Asn Arg Leu Gly Arg
            500                 505                 510

<210> SEQ ID NO 2
<211> LENGTH: 45
<212> TYPE: DNA
<213> ORGANISM: Rhabdovirus

<400> SEQUENCE: 2
```

-continued

```
tatatgctag cttattatta tcggagaacc aagaatagtc caatg                45

<210> SEQ ID NO 3
<211> LENGTH: 58
<212> TYPE: DNA
<213> ORGANISM: Rhabdovirus

<400> SEQUENCE: 3
aggatgttcg aaagcgtaat ctggtacatc atacggatac ttgcaattca ccccaatg  58
```

RECOMBINANT RHABDOVIRUS CONTAINING A HETEROLOGOUS FUSION PROTEIN

This application claims priority of copending provisional application No. 60/068,472 filed on Dec. 22, 1997.

FEDERAL SUPPORT

This invention arises in part from the following federal grants, and as a result the government may be entitled to certain rights under 37 C.F.R. §401: NIH GM53726.

FIELD OF THE INVENTION

This invention relates to a recombinant Rhabdovirus that expresses at least a fusion protein which facilitates fusion and entry of the recombinant Rhabdovirus into a cell target. This invention includes a recombinant Vesicular Stomatitis Virus (VSV) which expresses a fusion protein on the surface of the VSV particle. These recombinant Rhabdoviruses which express a fusion protein can be used to study function and specificity of proteins not naturally found on the Rhabdovirus being engineered, and as a method of targeting abnormal and diseased cells (e.g., virus infected cells or cancer cells) for diagnostic and therapeutic purposes. This invention also discloses methods of producing recombinant Rhabdoviruses.

BACKGROUND OF THE INVENTION

A. Using Viruses to Target Cells

Viruses have been engineered in the last decade to target cells, mainly for purposes of gene therapy. Gene therapy involves the delivery of a gene, often a diseased cell, and usually involves insertion of the gene into the genome of the host cell. Viruses from the families of Adenoviridae, Parvoviridae and Retroviridae have successfully been engineered not only to insert genes to cell genomes, but also to deliver the gene to specific cells or tissues.

To deliver viruses to specific cells, the virus must be able to infect that cell type. Viruses cannot typically infect all cells or even all organisms. The ability of a virus to infect a cell is based on the "tropism" the virus has for the host organism and the cells of that organism. For a virus to be able to infect a cell, the cell must have a receptor for a virus protein which allows the virus to recognize and bind to the cellular receptor, whereupon it enters the cell either via endocytosis, phagocytosis or macropinocytosis. Upon entry into the cell, the virus begins replicating. To infect cells for which the virus does not have a tissue tropism, the virus must be engineered to recognize and bind to a receptor on the cell or tissue of interest. Even then, a virus may still not be able to replicate, as it may require additional cellular factors not produced in that cell.

Gene therapy viral vectors typically do not kill or lyse the cells they target. Viral vectors used for gene therapy are engineered to deliver therapeutically effective DNAs with relative safety, like a drug (see for example, D. T. Curiel et al., U.S. Pat. No. 5,547,932). Some of these vectors are capable of replicating upon infection, but only in the targeted cells (F. McCormick, U.S. Pat. No. 5,677,178). Other gene therapy vectors are engineered such that they are unable to replicate. Non-replicating gene therapy vectors are usually produced using helper plasmids (see for example, G. Natsoulis, U.S. Pat. No. 5,622,856; M. Mamounas, U.S. Pat. No. 5,646,034) or packaging cells that confer genetic elements missing in the virus genome.

Gene therapy vectors have also encountered problems with overcoming the wild-type tropisms natural to the viral vector being utilized. Pseudotype viruses were created to overcome this by engineering a virus genome to contain the DNA encoding an envelope protein from another virus, even from a different virus family or genus, that would be capable of infecting the tissue or cell target. In recent years, many gene therapy patents have been issued describing adenovirus vectors (M. Cotten et al., U.S. Pat. No. 5,693,509); adeno-associated virus vectors (J. S. Lebkowski et al., U.S. Pat. No. 5,589,377); retrovirus vectors (B. O. Palsson et al., U.S. Pat. No. 5,616,487); vectors containing chimeric fusion glycoproteins (S. Kayman et al., U.S. Pat. No. 5,643,756); vectors that contain an antibody to a virus coat protein (Cotten et al.); viruses have been engineered to allow study of human immunodeficiency type 1 (HIV-1) in monkeys, a species that normally cannot be infected by HIV-1, by creating hybrid viruses (J. Sodroski et al., U.S. Pat. No. 5,654,195); and pseudotype retrovirus vectors which contain the G protein of Vesicular Stomatitis Virus (VSV) (J. C. Burns et al., U.S. Pat. Nos. 5,512,421 and 5,670,354). Some of these gene therapy vectors use methods which attempt to overcome some aspects of the tropism related problems encountered, while maintaining the efficacy of the vector for use in gene therapy.

Virus delivery vehicles have also been created for transient gene therapy, wherein expression of the gene delivered to the cell is transient and not permanent (I. H. Maxwell et al., U.S. Pat. No. 5,585,254). Vectors have been created that selectively express certain toxin-encoding genes, such as the gene for diphtheria toxin (U.S. Pat. No. 5,585,254.). Viral vectors also can be engineered to make the host cells they infect more immunogenic (U.S. Pat. No. 5,580,564).

B. Using Rhabdoviruses to Target Cells

Both Vesicular Stomatitis Virus (VSV) and Rabies Virus (RV) are members of the Rhabdoviridae family. VSV belongs to the Vesiculovirus genus, while RV belongs to the Lyssavirus genus. All members of the Rhabdovirus family possess lipid membrane envelopes which comprise the surface of the Rhabdovirus virion.

(1) Rabies Virus

A recent paper by T. Mebatsion et al. described the engineering of a Rabies Virus (RV) such that either the entire G protein was deleted or only a small portion of the G protein was expressed. This recombinant RV was further engineered such that either CD4 or CD4 and the CXCR4 co-receptor also were expressed on the envelope of the recombinant RV virion (T. Mebatsion et al., (1997) *Cell* 90: 941–951). Characterization of and experiments with these engineered RV pseudotype viruses demonstrated that a CD4/CXCR4 construct, which also contained the tail of the G protein, could infect cells expressing the HIV-1 envelope protein, gp120. A drawback of this viral system was that effective incorporation of the non-RV proteins (e.g., CD4 and CXCR4) only occurred when at least the tail of the G protein (a 44 amino acid cytoplasmic domain) was expressed on the virion in the form of a chimera fused to either CD4 (RV-CD4) or CXCR4 (RV-CXCR4). A recombinant RV expressing only the RV-CD4 and the truncated G protein chimera cDNA did not contain detectable amounts of CD4 in the virion. However, a recombinant RV expressing both RV-CD4 and RV-CXCR4 yielded a virus particle with both the CD4 and CXCR4 proteins in the virus envelope (T. Mebatsion et al., 1997). The authors' conclusion was that CD4-derived proteins are incorporated only in the form of a complex with a heterologous "carrier" protein. The carrier protein in the RV construct is the CXCR4 co-receptor.

(2) Vesicular Stomatitis Virus

CD4 also has been expressed in VSV particles along with all five VSV gene products: N, P, M, G and L (Schnell et al., (1996) *Proc. Nat'l Acad. Sci. USA* 93: 11359–11365). A more recent publication by Schnell et al., demonstrated that both CD4 and a co-receptor protein, such as CXCR4, can be expressed in virus particles even if the entire gene encoding the G protein is deleted (ΔG) (Schnell et al., (1997) *Cell* 90: 849–857). This CD4/CXCR4 recombinant was produced by utilizing a complementing plasmid containing DNA encoding the G protein. The gene encoding CXCR4 was then placed downstream of the gene encoding CD4 in the ΔG recombinant VSV. Levels of the ΔG-CD4 virus were 25% of the levels reported for the CD4 construct which contained the G protein (Schnell et al., 1997). However, CD4 was incorporated in the recombinant virion with the same efficiency as other VSV proteins despite the absence of a G protein. When comparing the ability of the ΔG-CD4 construct to infect HIV-1 infected Jurkat cells to the VSV ΔG construct containing both CD4 and CXCR4 (ΔG-CD4/CXCR4), the ΔG-CD4 construct infected the cells at 10% the rate of the ΔG-CD4/CXCR4 VSV recombinant. Moreover, the ΔG-CD4/CXCR4 was able to reduce the number of HIV-1 positive cells. These constructs were demonstrated to be capable of entering and propagating in cells infected with HIV-1 or that express the HIV-1 envelope protein (Schnell et al., 1997).

Although VSV and RV are members of the same virus family, Rhabdoviridae, VSV can produce an infectious virus particle in the absence of any G protein. In contrast, the RV recombinants could only function if the non-RV proteins were presented as a chimera containing the G tail fused to the non-VSV protein (Mebatsion et al., 1997). The ability to express a non-VSV protein in the lipid envelope of the VSV virion by itself and not as a chimera allows for the greater likelihood that the non-VSV protein, such as CD4, will form the same three-dimensional conformation that is found on the cell surface.

(3) Recombinant VSV with a Non-VSV Coreceptor Protein

A drawback of using the recombinant Rhabdoviruses as described by Mebatsion et al. (1997) and Schnell et al. (1997) is that in both cases they require a co-receptor protein, such as CXCR4 (derived from human T lymphocytes) for efficient infection into HIV-1 infected cells. The Mebatsion et al. (1997) recombinant RV virus additionally requires the tail of the G protein.

(4) Viral Envelope Fusion Proteins

The penetration of an enveloped virus into a cell occurs as a consequence of fusion of the viral envelope with the plasma membrane or with an intracellular compartment such as the endosome or lysosome following endocytosis. The fusion (F) protein of the paramyxovirus simian virus 5 (SV5) mediates a fusion between the viral envelope and the cell membrane. It has been cloned and expressed in recombinant cells. Other virus envelope proteins, including the G protein of VSV, require acid pH for fusion activity in vitro, and, in contrast, the Paramyxovirus SV5 F protein is capable of causing cell fusion at neutral pH. The wild-type virus fuses to its target cell through the combined action of the F protein and the associated HN protein of paramyxovirus. Cells that are transformed to express both the F protein and the HN protein can fuse with adjacent cells to form syncytia. However, vesicles created in vitro and comprising the F protein will not fuse with a target cell unless either the viral HN protein is also present or some other antireceptor molecule such as a lectin (i.e., wheat germ agglutinin) is present. R. G. Paterson et al., (1985) *Proc. Nat'l Acad. Sci. USA* 82: 7520–7524.

SUMMARY OF THE INVENTION

The present invention relates to recombinant or genetically engineered Rhabdoviruses that express a heterologous "F Protein" (as defined herein) to facilitate fusion of the lipid envelope of the recombinant virus to the cell membrane of a target cell. Such constructs overcome the limitations of systems known in the art that require specific co-receptors or exhibit specific target cell tropisms.

This invention relates to a recombinant Rhabdovirus comprising at least a heterologous F Protein or polypeptide fragment thereof that is effective to facilitate the fusion of the recombinant virus to a target cell membrane. A preferred embodiment of the invention uses the F protein of Paramyxovirus strain SV5 or a polypeptide fragment thereof as the F Protein as defined herein. The preferred recombinant Rhabdovirus can be Vesicular Stomatitis Virus (VSV) or Rabies Virus (RV). In the instance of Rabies Virus, the DNA encoding the Fusion Protein is preferably fused to a cDNA encoding a portion of the RV G protein, particularly the "tail" portion thereof.

The recombinant Rhabdoviruses contemplated by this invention may further express a second heterologous (i.e, another non-Rhabdovirus, non-RV or non-VSV protein). This heterologous protein may be used as an attachment protein or antireceptor to target the recombinant virus to a particular receptor present on the cell membrane of the target cell. Such heterologous attachment proteins preferably recognize and bind specifically to glycoproteins or proteins that are expressed on diseased or abnormal cells as part of the disease process. A preferred attachment protein is the CD4 protein, or derivatives thereof, that function to target a recombinant Rhabdovirus to cells infected with HIV that express GP120 proteins on their cell membranes. Other receptor proteins expressed on diseased or abnormal cells, to which corresponding attachment proteins may be expressed by an engineered Rhabdovirus according to the present invention, may result from conditions relating to a parasitic infection, a viral infection, a bacterial infection, neoplasia, pre-neoplasia, leukoplakia, polyps, dermatological conditions (e.g., café au lait spots) and benign tumors.

The present invention further relates to a method of producing a recombinant Rhabdovirus which expresses an F Protein or polypeptide fragment thereof effective to facilitate fusion of the Rhabdovirus to a cell membrane. The method includes the steps of: (A) inserting a cDNA encoding Rhabdovirus N, P, L and G proteins into a suitable cell; (B) inserting a polycistronic cDNA copy of the Rhabdovirus genome containing at least the 3' and 5' Rhabdovirus leader and trailer regions containing the cis acting signals for Rhabdovirus replication, the genes encoding the N, P, M, and L Rhabdovirus proteins and a gene encoding an F Protein or polypeptide fragment thereof into the suitable cell; (C) culturing the cell under conditions that permit production of the recombinant Rhabdovirus; and (D) isolating said recombinant Rhabdovirus.

The foregoing method may further comprise a means of expressing another non-Rhabdovirus protein or polypeptide fragment thereof. This additional heterologous protein will usually serve as an attachment protein and therefore should have the ability to recognize and bind to a receptor expressed on the cell membrane to which the engineered Rhabdovirus is to be targeted. One preferred embodiment of this method would be to express the F protein of paramyxovirus SV5 strain as the Fusion Protein of the engineered virus Another aspect of the present invention relates to a method of producing a recombinant Rhabdovirus which expresses an F Protein or a polypeptide fragment thereof effective to facilitate fusion of the Rhabdovirus to a cell membrane. This method includes the steps of: (A) inserting into suitable cells a polycistronic cDNA comprising at least the 3' and 5' Rhabdovirus leader and trailer regions containing the cis acting signals for Rhabdovirus replication, the genes encoding the Rhabdovirus N, P, and L proteins and a gene encoding an F Protein or polypeptide fragment thereof; (B) infecting the cells with a minivirus comprising the cis acting signals for Rhabdovirus replication and genes encoding at least the Rhabdovirus G and M proteins; (C) culturing the cells under conditions to permit expression of the cDNA to produce the recombinant Rhabdovirus; and (D) isolating said recombinant Rhabdovirus.

Preferred recombinant Rhabdoviruses would be VSV and RV.

The method of targeting diseased cells either in vivo or in vitro with a recombinant Rhabdovirus expressing a fusion protein comprises the steps of contacting the target diseased or abnormal cell with the recombinant Rhabdovirus under conditions that would permit infection by the recombinant virus. This embodiment may require the additional expression of another non-Rhabdovirus protein on the surface of the virus particle to serve as an attachment protein or antireceptor. Said cell targeting by a recombinant Rhabdovirus may further consist of expression of a reporter protein or fluorescent protein upon infection of the targeted cell. The targeted cell may additionally be diseased or infected. One recombinant Rhabdovirus contemplated would be one which expresses the F protein of Paramyxovirus SV5 as mediating the step of fusion.

The recombinant Rhabdoviruses described above are further contemplated for treating a subject suffering from a viral, parasitic or bacterial infection comprising administering to a patient a therapeutically effective amount of the recombinant Rhabdovirus that expresses the fusion protein. This recombinant Rhabdovirus ideally would be able to recognize and differentiate the cells infected with a virus, bacteria or parasite from those that are uninfected. It would bind to a protein expressed on the cells which arises as a result of the infection. The non-Rhabdovirus (attachment) protein responsible for binding to the infected cells is operatively linked to the regulatory sequences of the recombinant Rhabdovirus genes. Said method is similarly contemplated for treating a subject suffering from a disease, wherein the non-Rhabdovirus protein expressed by the recombinant Rhabdovirus expressing a fusion protein is capable of recognizing and binding to the protein expressed on the surface of the diseased or abnormal cell. The diseased or abnormal cell or tissue contemplated for treatment includes neoplastic cells, pre-neoplastic cells, benign tumors, polyps, cafe au lait spots, leukoplakias, other skin moles or lesions or dermatologic conditions.

The invention also relates to a method of identifying Fusion Proteins as defined herein. Steps of this method include: (A) inserting suitable cells with a polycistronic first cDNA containing at least the 3' and 5' Rhabdovirus leader and trailer regions containing the cis acting signals for Rhabdovirus replication, the Rhabdovirus genes encoding the N, P, and L proteins, a gene encoding an F Protein candidate and a non-Rhabdovirus protein; (B) infecting the cells with a minivirus containing cis acting signals for Rhabdovirus replication and a second cDNA encoding a reporter protein; (C) culturing the cells under conditions to permit replication of the first and the minivirus to produce a recombinant Rhabdovirus; (D) isolating said recombinant Rhabdovirus; (E) bringing the isolated recombinant Rhabdovirus in contact with uninfected cells under conditions permitting infection by said recombinant Rhabdovirus; and (F) determining whether the reporter protein is expressed.

BRIEF DESCRIPTION OF THE DRAWING FIGURES

FIGS. 1A and B. Quantitation of particle production and glycoprotein incorporation by Western blot analysis.

Figure 2A:
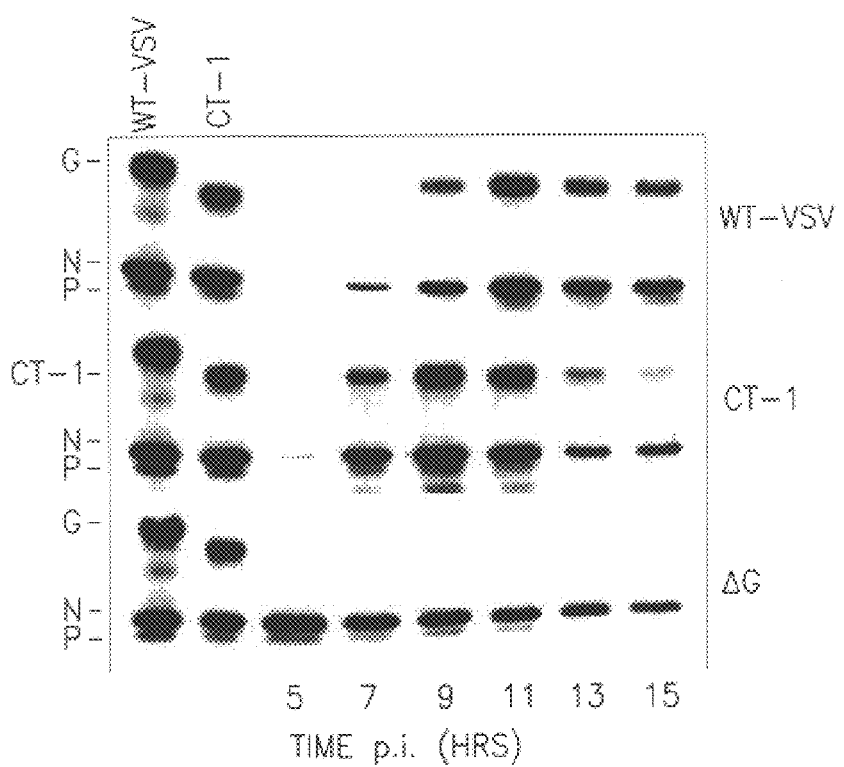
Figure 2B:
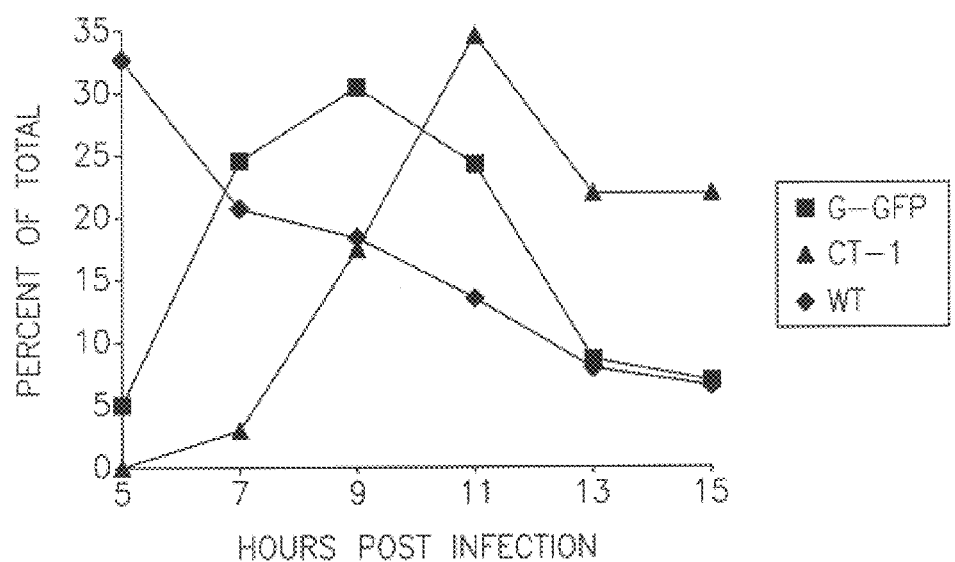

FIGS. 2A and 2B. Budding profiles of wt-VSV, CT-1 and ΔG viruses.

Figure 3:
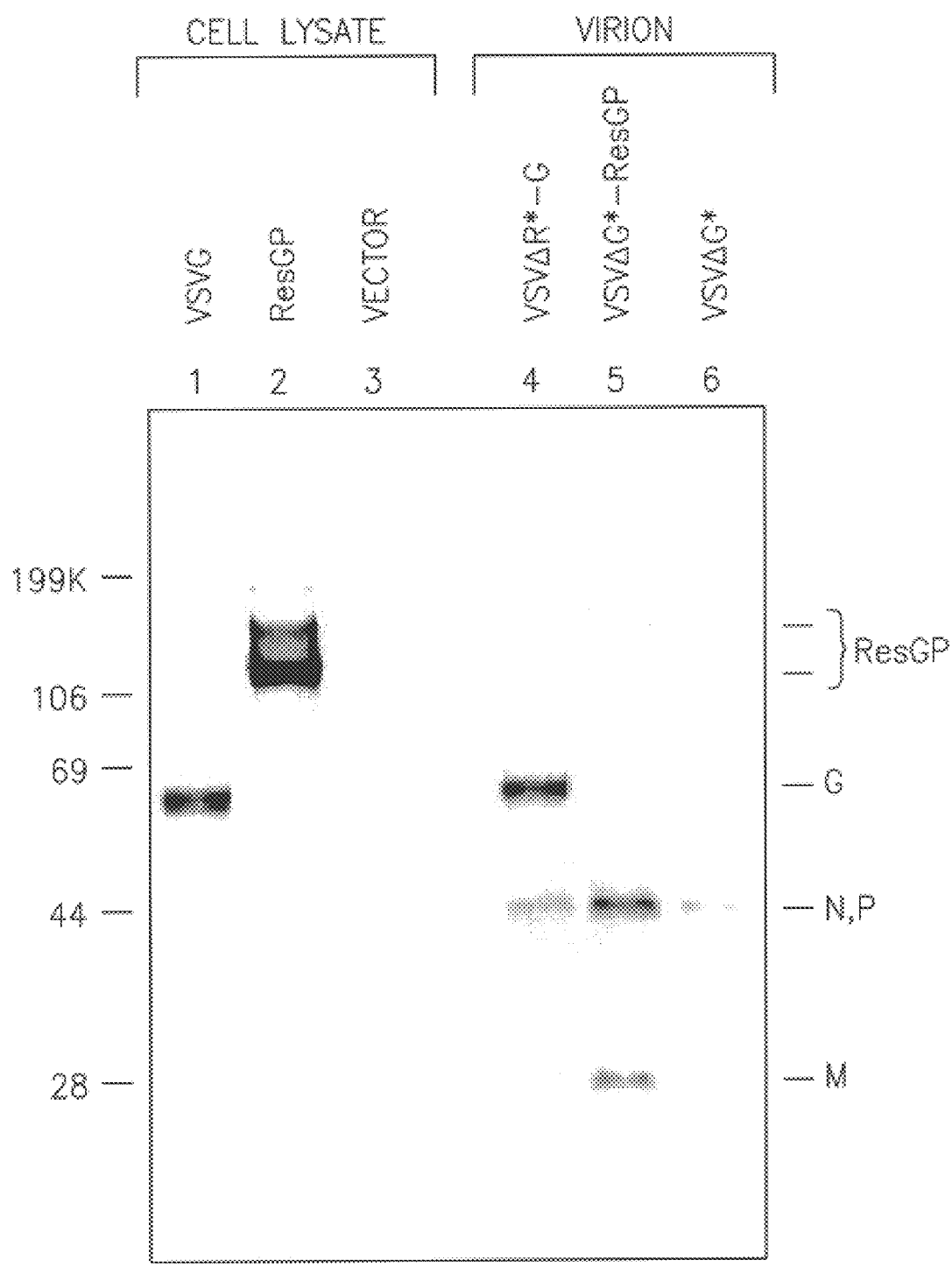

FIG. 3. Incorporation of ResGP into VSV particles.

Figure 4:
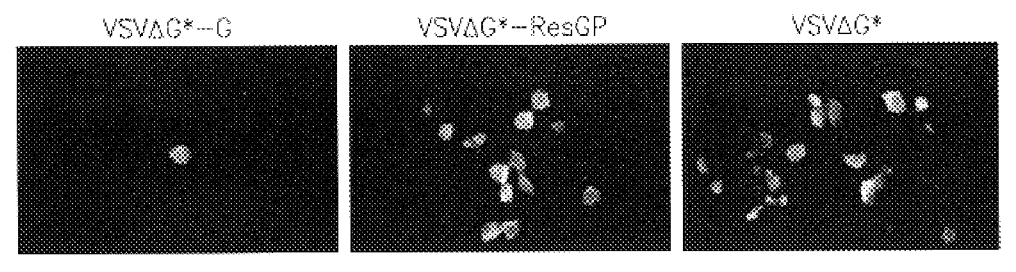

FIG. 4. Expression of Green Fluorescent Protein (GFP) upon infection with recombinant VSVs. Vero cells were infected with VSV ΔG*-G, VSV ΔG*-ResGP or VSV ΔG*, and GFP expression was examined 12 hours after infection by fluorescence microscopy.

Figure 5:
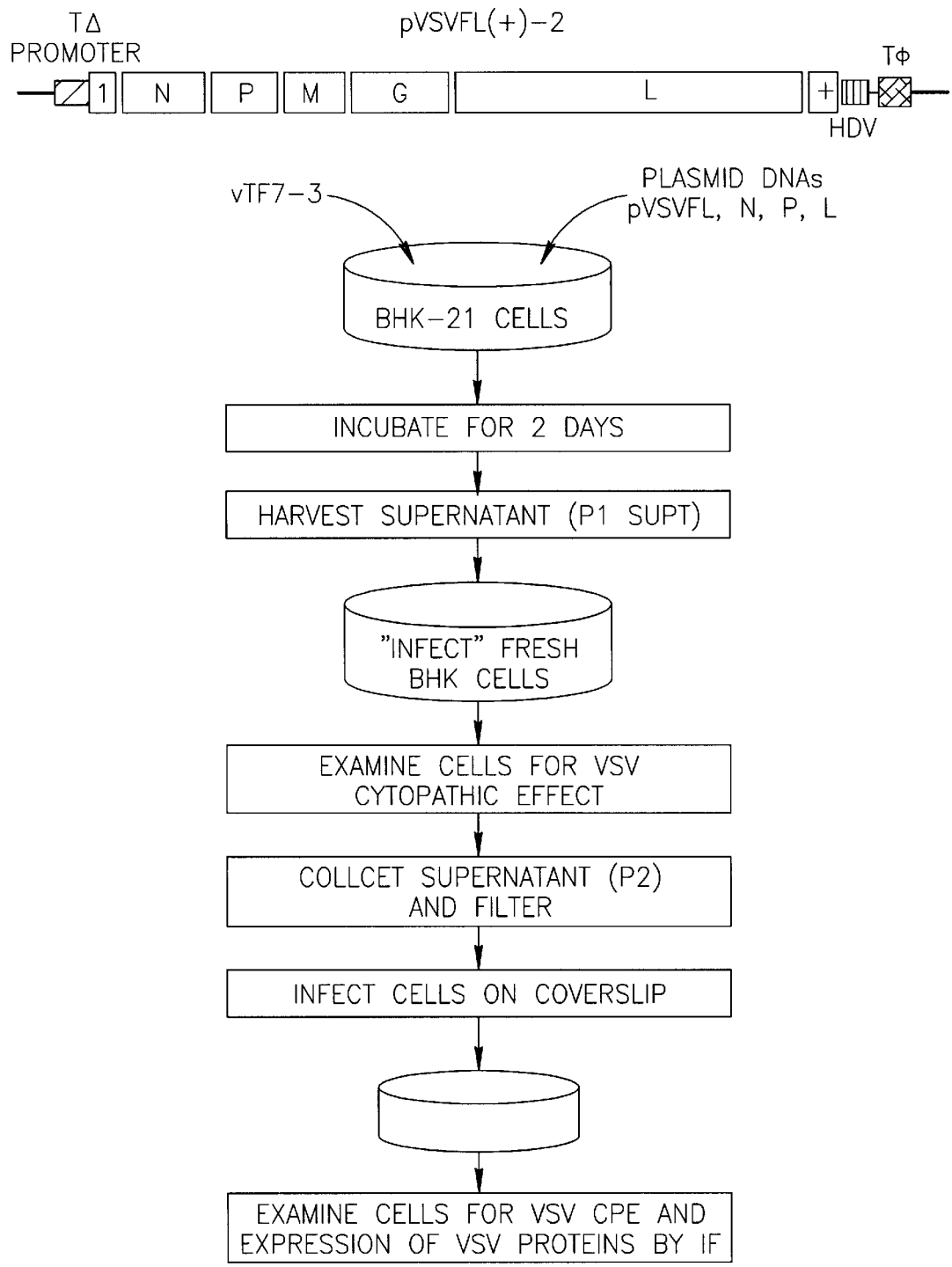

FIG. 5. Diagram of the Method of Recovering Infectious Recombinant VSV from Plasmids. Recovery of infectious particles is performed by infecting $10^6$ BHK-21 cells with vTF7-3 for 60 minutes and then the cells are transfected with 10 μg of plasmid encoding the various full-length VSV constructs and 3 μg, 5 μg, and 1 μg of plasmids encoding the $VSV_{Ind}$ nucleocapsid protein (N), phosphoprotein (P), and polymerase (L), respectively. Cells are incubated for two days to allow replication and assembly of viral particles. The supernatant from the cells is then plated directly onto fresh BHK cells, and the cells are incubated for 24 hr to permit virus amplification. The supernatant from these cultures is then passed through a 0.2μ filter (Millex-GS, Millipore) to remove vaccinia virus and 1 ml of the filtered supernatant is transferred onto fresh BHKs. Following an one hr absorption, the supernatant is replaced with DMEM-FCS. The media of cultures exhibiting the cytopathic effects (CPE)of a VSV infection are then removed and the virus is plaque purified. Virus stocks are subsequently prepared by infection of $10^7$ cells with approximately $10^5$ plaque forming units (p.f.u.) of the plaque isolate. The supernatant from these cultures is then used for all subsequent infections. Direct sequencing of the viral RNA isolated from every recovered virus is performed to ensure the recovered virus is derived from the plasmid (see Example 1).

Figure 6:
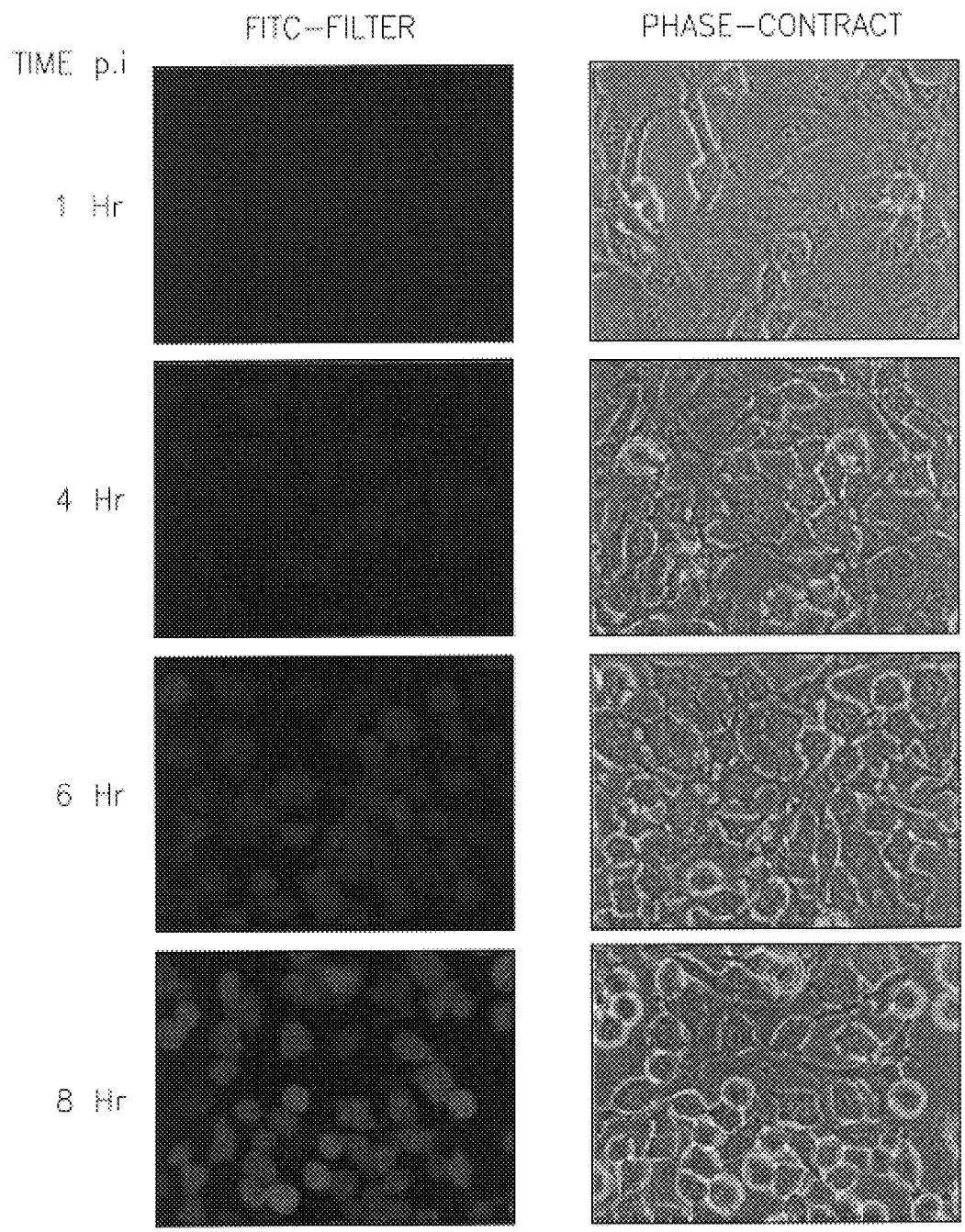

FIG. 6. Time course for GFP expression in ΔG-GFP infected cells and infectivity of recombinant CD4-VSV pseudotyped with the SV5 F protein on cells expressing HIV gp160.

Figure 7:
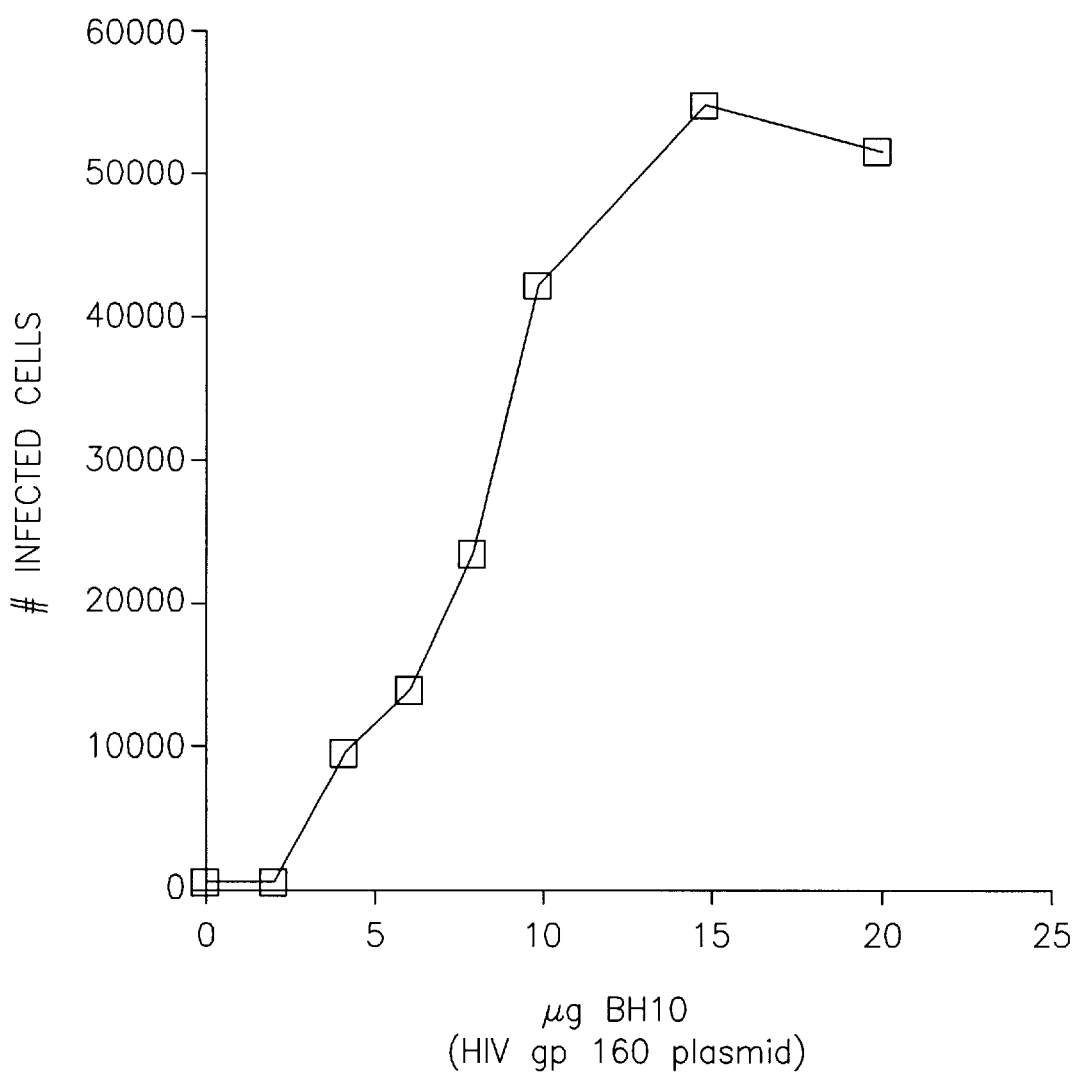

FIG. 7. Infectivity of recombinant CD4-VSV pseudotyped with the SV5 F protein on cells expressing HIV gp160.

Figure 8:
Figure 8:
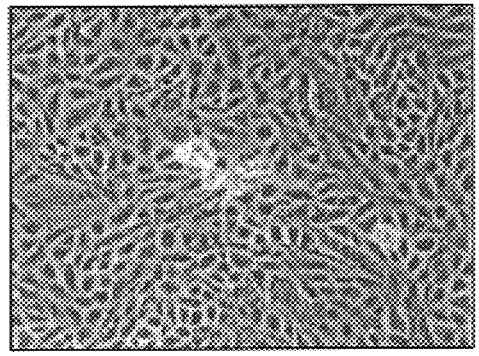
Figure 8:
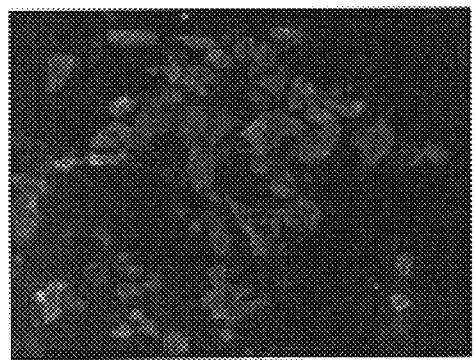
Figure 8:
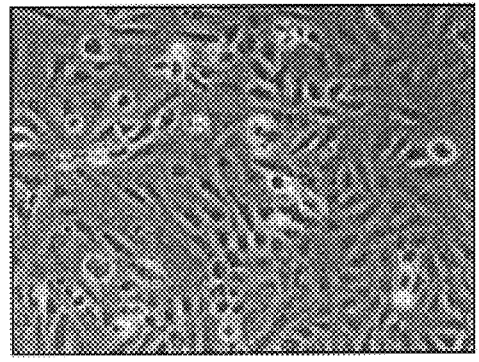
Figure 8:
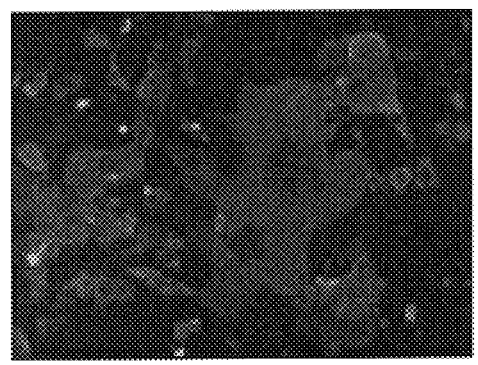
Figure 8:
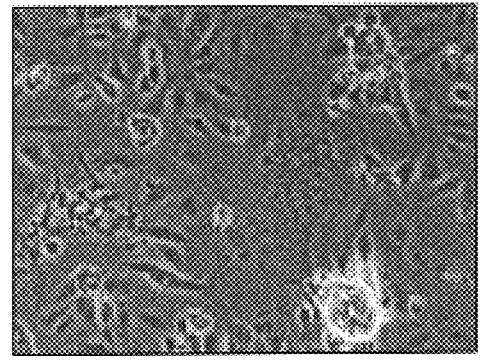

FIG. 8. Infectivity of VSV-CD4 Recombinants. The right-hand column displays the cells under phase contrast microscopy. The left-hand column displays the cells infected with the VSV-CD4 recombinants which are detected using an anti-VSV N protein antibody and immunofluorescence microscopy. The upper panels are cells exposed to VSVCD4-G. The middle panels are cells which have been exposed to the VSV/CD4-Q427 recombinant. The lower panels are cells which have been exposed to VSV/HAGS/CD4-G.

Figure 9:
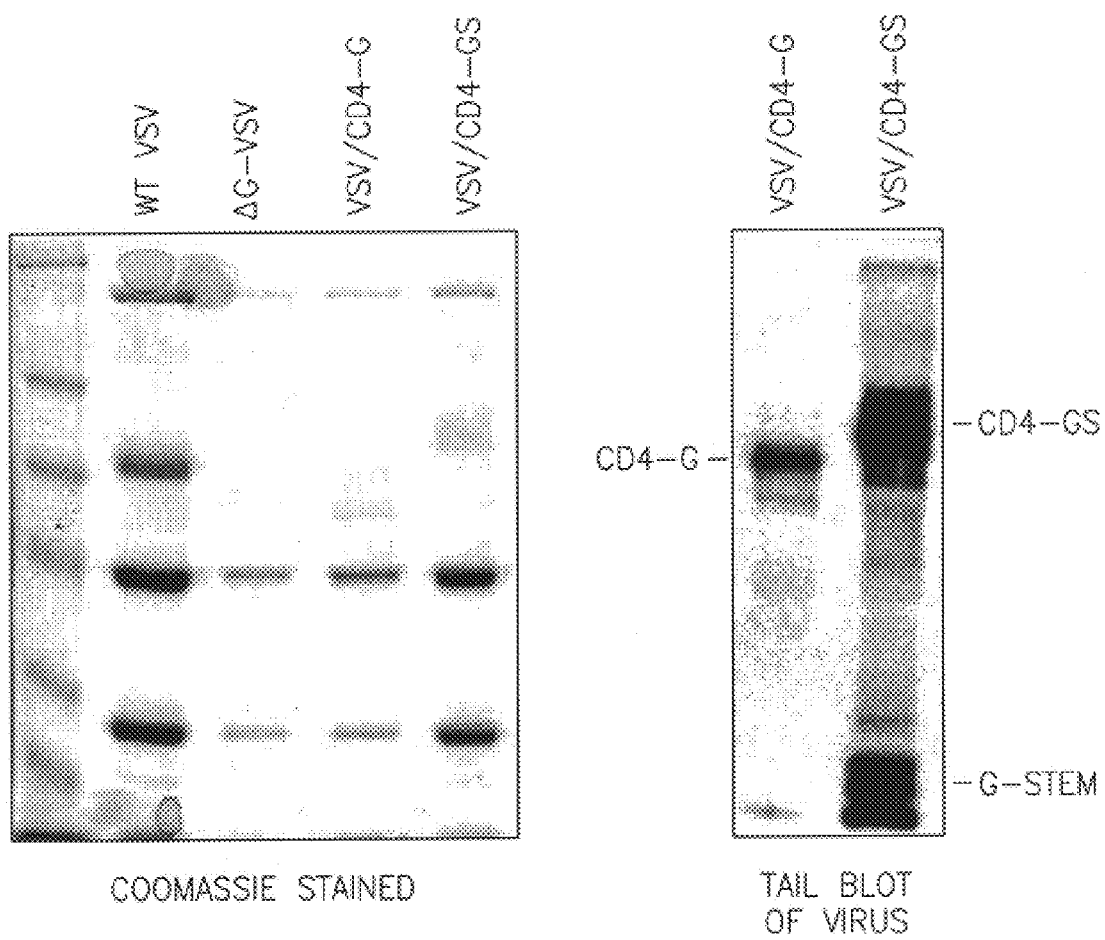

FIG. 9. Virus Production and G-stem incorporation. The left-hand panel displays the proteins of the different recombinant VSV constructs which have been separated on SDS-PAGE and stained with Coomassie blue. The right-hand panel is a Western blot wherein the G protein was detected using an antibody which recognizes the cytoplasmic domain of the VSV G protein. Therefore, the G stem, the heterologous protein CD4-G and CD4-GS are all detected by this antibody.

Figure 10:
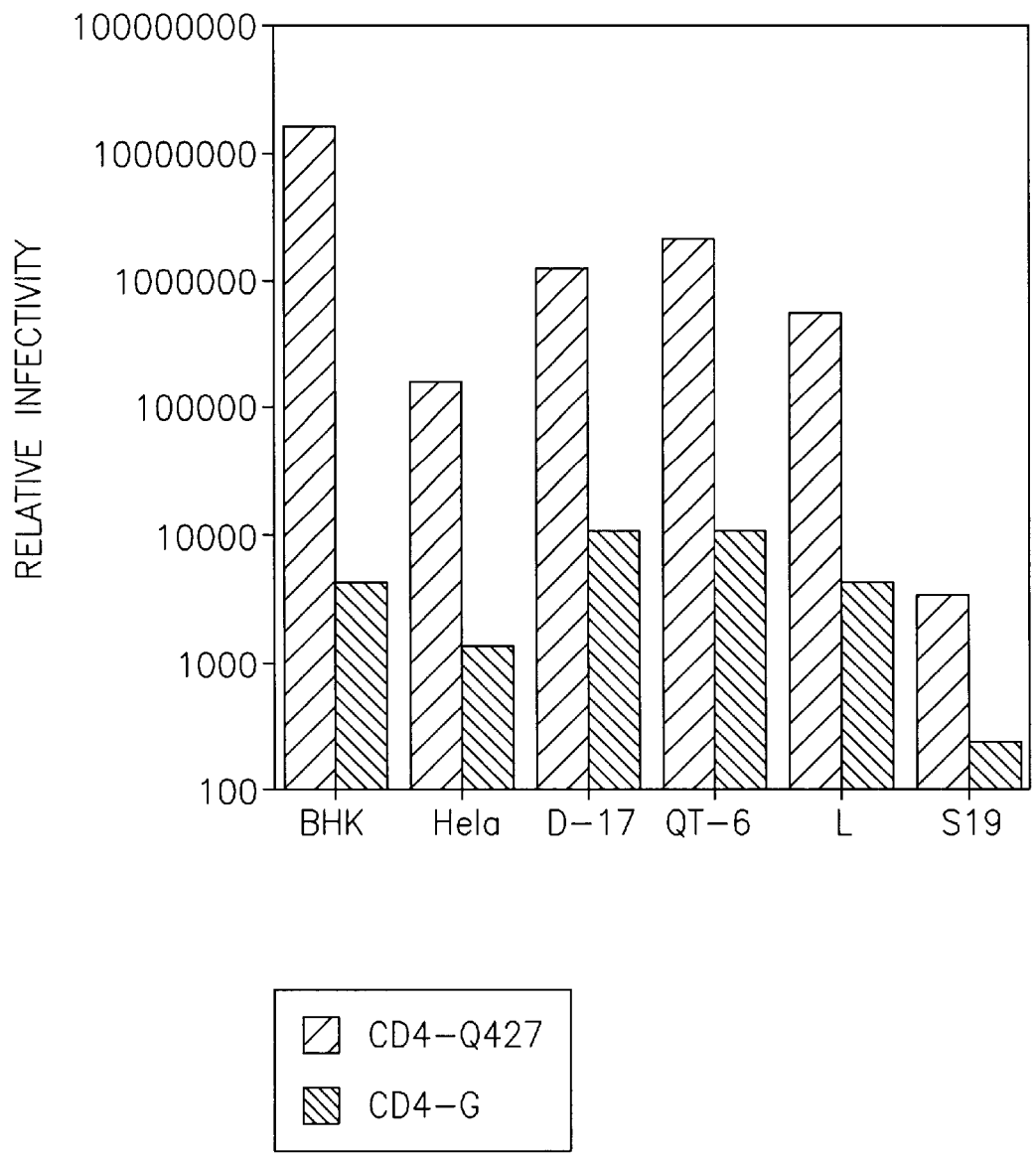

FIG. 10. Infectivity of VSV/CD4-GS virions produced from various cell lines for infecting HXB2 Cells. Infectivity of the CD4-Q427 and CD4-G recombinants were tested in BHK, HeLa (Hela), D-17, QT-6, L and Sf9 cells. The relative infectivity was higher for the G stem construct (e.g., CD4-Q427) than in the CD4-G construct which expresses the entire VSV G protein.

DETAILED DESCRIPTION

A. Making Recombinant Rhabdoviruses (1) Fusion Proteins

As used herein, the term "Fusion Protein" or "F Protein" means any protein (or fusion-facilitating polypeptide fragment thereof) that: (1) is derived from a virus characterized as having a lipid envelope; and (2) when expressed as a heterologous protein in a genetically engineered virus facilitates the fusion of the viral envelope to a cell membrane, where such fusion is mediated by the binding of an attachment protein (or "antireceptor") on the viral envelope to a receptor on the cell membrane. It is thus contemplated that an F Protein according to the present invention can function in a non-specific fashion in facilitating the association of an attachment protein on the viral envelope other than the native viral attachment protein. One example of an F Protein as contemplated herein is the viral envelope fusion protein known in the literature as the "F protein" of the SV5 strain of Paramyxoviruses which specifically is referred to herein as the "F protein" rather than the more generic "F Protein" or "Fusion Protein."

An "antireceptor," also referred to as an "attachment protein," means the protein on a viral envelope that is responsible for the step of attaching a virus particle to the corresponding "receptor" on the cell membrane. For example, the native antireceptor of the paramyxovirus SV5 F protein is the viral HN protein.

"Virus attachment" means the step that occurs in the process of infecting when the antireceptor on the lipid envelope of the virus particle recognizes and binds a cell surface "receptor." The skilled artisan will recognize that virus attachment is a prior step before the fusion of the viral envelope membrane with the target cell's plasma membrane occurs. Fusion is a prior step before the virus particle penetrates the cell.

(2) Rhabdoviruses Used

The "Rhabdoviruses" contemplated for use in this invention include viruses from the Vesiculovirus genus and the Lyssavirus genus. The Vesiculovirus genus includes: Vesicular Stomatitis Virus (VSV) New Jersey serotype ($VSV_{NJ}$), VSV-Indiana serotype ($VSV_{Ind}$), VSV-Alagoas strain, Cocal virus, Jurona virus, Carajas virus, Maraba virus, Piry virus, Calchaqui virus, Yug Bogdanovac virus, Isfahan virus, Chandipura virus, Perinet virus, and Porton-S virus (R. R. Wagner et al., In B. N. Fields' Virology 3rd ed. vol. 1 (1996)). The Lyssavirus genus includes: Rabies virus (RV), Lagos bat virus, Mokola virus, Duvenhage virus, Obodhiang virus, and Kotonkan virus (Id.). The preferred recombinant Rhabdoviruses would be VSV (any serotype or strain) and RV (Id.).

All Rhabdoviruses contain five genes which encode the nucleocapsid (N) protein, Phosphoprotein (P, but was originally designated NS), matrix (M) protein, glycoprotein (G) and large protein (L) proteins. These genes are ordered on a genomic RNA that is negative sense and ordered as follows: 3'-N-P-M-G-(X)-L-5'. The order of the genes is important as it dictates the proportion of proteins synthesized. Any manipulation of a Rhabdovirus genome must maintain at least five transcription domains in order to maintain full capability to infect and replicate. Rhabdoviruses have an endogenous RNA polymerase for transcription of plus sense messenger RNA (mRNA). The X gene does not occur in all Rhabdoviruses. The X gene encodes a nonstructural protein found in the fish infectious hematopoietic necrosis virus, a nonstructural glycoprotein in the bovine ephemeral fever virus and a pseudogene in the rabies virus. The extra (X) gene has been found in different locations on the Rhabdovirus genome. Synthesis of the M protein in infected cells is cytopathic to the cell, and will eventually result in cell death.

A "recombinant Rhabdovirus" means a virus that expresses proteins not native to the Rhabdovirus. This creates a "pseudotype" or "chimeric" virus. By "minivirus" is meant an incomplete virus particle containing the polycistronic nucleic acid molecule encoding N-P-M-L, N-P-L, N-P-G-L, M-G, G only, M only or any combination of four or fewer VSV genes. This incomplete virus particle does not have the capacity to replicate.

A "recombinant Rhabdovirus" or "recombinant VSV" or "recombinant RV" means any recombinant Rhabdovirus including VSV and RV produced by transfection of a cDNA or cDNAs that contains at least a fusion protein or polypeptide fragments thereof. Recombinant Rhabdoviruses produced by the transfection of cDNA or cDNAs may also be complemented in trans with a minivirus or additional cDNA with which to make an infectious virus particle. Alternatively, the proteins can be supplied using a helper cell which stably expresses the proteins needed to produce a functional virus particle.

By "polypeptide fragment" is meant a fragment of a protein, antibody, antireceptor, receptor, Rhabdovirus protein, VSV protein, etc., possessing biological activity, such as augmenting and/or enhancing virus particle fusion, augmenting and/or enhancing cell targeting, augmenting and/or enhancing virus titers and/or virus infectivity, etc.

A "non-Rhabdovirus protein" or "non-VSV protein" or "non-RV protein" means any protein or polypeptide fragment of that protein which is not naturally expressed in wild-type Rhabdovirus (or VSV or RV) which has been engineered to express the fusion protein.

An "infectious recombinant" means a recombinant Rhabdovirus produced by any of the described methods that after infection of a cell is capable of replicating new virus particles that in turn can infect other targeted cells. By "non-infectious recombinant" is meant a recombinant Rhabdovirus produced by any of the described methods that after infection of the target cell cannot release or produce new virus particles. For example, a "non-infectious recombinant" Rhabdovirus would comprise genes encoding the N, P and L proteins but lacking the genes encoding G and M proteins.

The recombinant Rhabdoviruses and VSV constructs described can further comprise an "enhancer protein" or a "G stem polypeptide" which is expressed on the envelope of the virus particle. By "G stem," "G stem polypeptide" or "enhancer protein" is meant a polypeptide comprising the cytoplasmic tail domain, the transmembrane domain and about 23 amino acids to about 70 amino acids of the carboxy terminus of the membrane proximal ectodomain of a Rhabdovirus G protein. Additional G stem polypeptides contemplated comprise similar regions from all G proteins of all VSV serotypes and all strains within those serotypes, as well as analogous G stem polypeptides from other Rhabdovirus G proteins. These G stem polypeptides are utilized to enhance recombinant virus titers and infectivity. Functionality of the G stem can be assessed by assaying envelope infectivity. Envelope infectivity is compared between a Rhabdovirus construct expressing an F Protein and an antireceptor and a Rhabdovirus construct expressing an F Protein and a G stem. The addition of a G stem can increase infectivity of the Rhabdovirus construct 100 to $10^8$ fold.

These G stem polypeptides can be expressed with an F Protein and an antireceptor proteins in the following combinations: (1) a G stem polypeptide, an F Protein and an antireceptor protein or a polypeptide fragment thereof, each expressed separately; (2) a separately expressed G stem polypeptide and an F Protein expressed from a common encoding DNA in open reading frame with the antireceptor protein; or (3) a separately expressed F Protein and an G stem polypeptide expressed from a common encoding DNA in open reading frame with an antireceptor protein.

One example of a VSV G stem polypeptide is the VSV G stem of VSV-Indiana strain (GenBank Accession No. 61834). G stem polypeptides starting after $VSV_{Ind}$ $^{336}N$ are contemplated herein. More preferred G stem polypeptides start after $VSV_{Ind}$ residue $^{392}T$. Most preferred G stem polypeptides can include from $^{404}Gly$ to $^{511}Arg$ ($^{404}$ghgmlds glhlsskaqv fehphiqdaa sqlpddeilf fgdtglsknp idfvegwfss wkssiasfff iigliiglfl vlrvgiylyi klkhtkkrqi ytdiemnrlg $r^{511}$). Another preferred $VSV_{Ind}$ G stem includes the polypeptide comprising $^{434}Pro$ to $^{511}Arg$ ($^{434}$pddeilf fgdtglsknp idfvegwfss wkssiasfff iigliiglfl vlrvgiylyi klkhtkkrqi ytdiemnrlg $r^{511}$). Other contemplated $VSV_{Ind}$ G stems include G stems starting after $^{404}Gly$ of the G protein. Less preferred are those $VSV_{Ind}$ G stems which start downstream from $^{440}Phe$, because although these G stems possess a high assembly phenotype, they have lower specific infectivity than G stem constructs which begin upstream from $^{440}Phe$. The $VSV_{Ind}$ G stems contemplated therefore comprise the entire cytoplasmic tail domain (the double underlined portion of the VSV-Indiana G protein) and all of the transmembrane domain (designated in capitalized, bold letters), as well as portions of the carboxy terminus of the membrane proximal ectodomain (e.g., at least 23 to about 127 amino acids of the carboxy terminus of the ectodomain), as described below (SEQ ID No: 1):

1 mkcflylafl figvnckfti vfphnqkgnw knvpsnyhyc psssdl-
   nwhn dligtglqvk
61 mpkshkaiqa dgwmchaskw vttcdfrwyg pkyithsirs ftps-
   veqcke sieqtkqgtw
121 lnpgfppqsc gyatvtdaea vivqvtphhv lvdeytgewv dsqf-
   ingkcs ndicptvhns
181 ttwhsdykvk glcdsnlist ditffsedre lsslgkegtg frsnyfayet
   gdkackmqyc
241 khwgvrlpsg vwfemadkdl faaarfpecp egssisapsq tsvd-
   vsliqd verildyslc
301 qetwskirag lpispvdlsy lapknpgtgp aftiingtlk yfe-
   tryirvd iaapilsrmv
361 gmisgttter elwddwapye dveigpngvl rtssgykfpl ymigh-
   gmlds glhlsskaqv
421 fehphiqdaa sqlpddeilf fgdtglsknp idfvegwfss wkS-
   SIASFFF IIGLIIGLFL
481 VL rvgiylyi klkhtkkrqi ytdiemnrlg r Other analogous G stem polypeptides from other serotypes or strains of VSV as well as other Rhabdoviruses comprising the above described domains would be readily apparent to the skilled artisan.

(3) Methods of Making Recombinant Rhabdoviruses Using cDNAs (i) The DNA Needed to Make a Recombinant Rhabdovirus The phrase "cDNA's necessary" to produce an infectious Rhabdovirus or a non-infectious Rhabdovirus means the nucleic acid molecules required to produce either infectious or non-infectious recombinant Rhabdovirus particles that express a fusion protein. These recombinant viruses can be produced (1) entirely using cDNAs or (2) a combination of cDNAs transfected into a helper cell, or (3) cDNAs transfected into a cell, which is further infected with a minivirus providing in trans the remaining components or activities needed to produce either an infectious or non-infectious recombinant Rhabdovirus. Using any of these methods (e.g., minivirus, helper cell line, or cDNA transfection only), the minimum components required are an RNA molecule containing the cis-acting signals for (1) encapsidation of the genomic (or antigenomic) RNA by the Rhabdovirus N protein, and (2) replication of a genomic or antigenomic (replicative intermediate) RNA equivalent.

By a replicating element or replicon, we mean a strand of RNA minimally containing at the 5' and 3' ends the leader sequence and the trailer sequence of a Rhabdovirus. In the genomic sense, the leader is at the 3' end and the trailer is at the 5' end. Any RNA placed between these two replication signals will in turn be replicated. The leader and trailer regions further must contain the minimal cis-acting elements for purposes of encapsidation by the N protein and for polymerase binding which are necessary to initiate transcription and replication.

For preparing engineered Rhabdoviruses or VSVs using a minivirus, the minivirus containing the G gene would also contain a leader region, a trailer region and a G gene with the appropriate initiation and termination signals for producing a G protein mRNA. If the minivirus further comprises a M gene, the appropriate initiation and termination signals for producing the M protein mRNA must also present.

For any gene contained within the engineered Rhabdovirus genome, the gene would be flanked by the appropriate transcription initiation and termination signals which will allow expression of those genes and production of the protein products.

To produce "non-infectious" engineered Rhabdovirus, the engineered Rhabdovirus must have the minimal replicon elements and the N, P and L proteins and it must contain the M gene (one example is the ΔG construct described in the examples below). This produces virus particles that are budded from the cell, but are non-infectious particles. To produce "infectious" particles, the virus particles must additionally comprise proteins that can mediate virus particle binding and fusion, such as through the use of an attachment protein or antireceptor. The native antireceptor of Rhabdoviruses is the G protein.

A "suitable cell" means any cell that would permit assembly of the recombinant Rhabdovirus for any one of the three methods disclosed below.

To prepare infectious virus particles, an appropriate cell line (e.g., BHK cells) is first infected with vaccinia virus vTF7-3 (T. R. Fuerst et al., (1986) *Proc. Nat'l Acad. Sci. USA* 3: 8122–26) or equivalent which encodes a T7 RNA polymerase or other suitable bacteriophage polymerase such as the T3 or SP6 polymerases (see Usdin et al., (1993) *BioTechniques* 14:222–224 or Rodriguez et al. (1990) *J. Virol.* 64:4851–4857). The cells are then transfected with individual cDNA containing the genes encoding the G, N, P, L and M Rhabdovirus proteins. These cDNAs will provide the proteins for building the recombinant Rhabdovirus particle. Cells can be transfected by any method known in the art (e.g., liposomes, electroporation, etc.). The cell line is also transfected with a cDNA encoding a fusion protein, such as the F protein of paramyxovirus strain SV5. A gene encoding a fusion protein can be transfected into the cells by itself or fused to a DNA encoding portion of the G protein tail. A fusion of the F protein to the G protein tail described by Mebatsion et al., (1997) would be required when preparing infectious or non-infectious recombinant RV virion.

Also transfected into the cell line is a "polycistronic cDNA" containing the Rhabdovirus genomic RNA equivalent. If the infectious, recombinant Rhabdovirus particle is intended to be lytic in an infected cell, then the genes encoding for the N, P, M and L proteins must be present as well as the gene encoding the fusion protein or polypeptide fragments thereof. If the infectious, recombinant Rhabdovirus particle is not intended to be lytic, then the gene encoding the M protein is not included in the polycistronic DNA. By "polycistronic cDNA" is meant a cDNA comprising at least transcription units containing the genes which encode the N, P and L proteins. The recombinant Rhabdovirus polycistronic DNA may also contain a gene encoding a fusion protein or polypeptide fragment thereof. Alternatively, the fusion protein or fragment thereof may be supplied in trans. Another embodiment contemplated is a polycistronic cDNA comprising a gene encoding a reporter protein or fluorescent protein (e.g., green fluorescent protein and its derivatives, β-galactosidase, alkaline phosphatase, luciferase, chloramphenicol acetyltransferase, etc.), the N-P-L or N-P-L-M genes, and a fusion protein. Another polycistronic DNA contemplated may contain a gene encoding an attachment protein, as well as a gene encoding a fusion protein, a gene encoding a reporter and either the N-P-L genes or the N-P-L-M genes. When engineering a recombinant RV, the genes encoding the fusion protein and the attachment protein would have to be fused to the G tail, as described by Mebatsion et al. (1997). The first step in generating a recombinant Rhabdovirus is expression of an RNA that is a genomic or antigenomic equivalent from a cDNA. Then that RNA is packaged by the N protein and then replicated by the P/L proteins. The virus thus produced can be recovered. If the G protein is absent from the recombinant RNA genome, then it must be supplied in trans. If both the G and the M proteins are absent, then both must be supplied in trans.

For preparing "non-infectious Rhabdovirus" particles, the procedure may be the same as above, except that the polycistronic cDNA transfected into the cells would contain the N, P and L genes of the Rhabdovirus only. The polycistronic cDNA of non-infectious Rhabdovirus particles may additionally contain a gene encoding a reporter protein. For additional description regarding methods of producing a recombinant VSV, which lacks the gene encoding the G protein, see A. Takada et al., (in press, 1997) *Proc. Nat'l Acad. Sci. USA*.

(ii) Culturing of Cells to Produce Virus

Transfected cells are usually incubated for at least 24 hr at the desired temperature, usually about 37° C. For non-infectious virus particles, the supernatant is collected and the virus particles isolated. For infectious virus particles, the supernatant containing virus is harvested and transferred to fresh cells. The fresh cells are incubated for approximately 48 hours, and the supernatant is collected.

(iii) Purification of the Recombinant Rhabdovirus

The terms "isolation" or "isolating" a Rhabdovirus means the process of culturing and purifying the virus particles such that very little cellular debris remains. One example would be to take the virion containing supernatant and pass them through a 0.1–0.2μ pore size filter (e.g., Millex-GS, Millipore) to remove the vaccinia virus and cellular debris (See Example 1). Alternatively, virions can be purified using a gradient, such as a sucrose gradient. Recombinant Rhabdovirus particles can then be pelleted and resuspended in whatever excipient or carrier is desired. Titers can be determined by indirect immunofluorescence using, for example, anti-M (23H12) or anti-N (10G4) protein specific antibodies (L. Lefrancois et al., (1982) *Virology* 121: 157–67).

(4) Methods of Making Recombinant Rhabdoviruses Using cDNAs and a Minivirus or a Helper Cell Line Both "miniviruses" and "helper cells" (also known as "helper cell lines") provide the same thing: to provide a source of Rhabdovirus proteins for Rhabdovirus virion assembly. One example of a Rhabdovirus minivirus is the VSV minivirus which expresses only the G and M protein, as reported by E. A. Stillman et al., (1995) *J. Virol.* 69: 2946–53. Helper viruses and miniviruses are used as methods of providing Rhabdovirus proteins that are not produced from transfected DNA encoding the genes for Rhabdovirus proteins.

When using a minivirus, cells are infected with vaccinia virus as described above for purposes of providing T7 RNA polymerase. The desired polycistronic RNA, and plasmids containing the N, P and L genes are transfected into cells. The transfection mix is removed after approximately 3 hrs, and cells are infected with the minivirus at a m.o.i. of about 1. The minivirus supplies the missing G and/or M proteins (see Stillman et al., (1995) *J. Virol.* 69: 2946–53.). The polycistronic RNA transfected into the cell will depend on whether an infectious or non-infectious recombinant Rhabdovirus is wanted.

Alternatively, a minivirus could be used to provide the N, P and L genes. The minivirus could also be used to produce the M protein in addition to N, P and L. The minivirus also can produce the G protein.

When using a helper cell line, the genes encoding the missing Rhabdovirus proteins are produced by the helper cell line. The helper cell line has N, P, L and G proteins for production of recombinant Rhabdovirus particles which does not encode wild-type G protein. The proteins are expressed from genes or DNAs that are not part of the recombinant virus genome. These plasmids or other vector system is stably incorporated into the genome of the cell line. The proteins are then produced from the cell's genome and not from a replicon in the cytoplasm. The helper cell line can then be transfected with a polycistronic DNA and plasmid cDNAs containing the other Rhabdovirus genes not expressed by the helper virus. The polycistronic RNA used will depend on whether an infectious or non-infectious recombinant Rhabdovirus is desired. Otherwise, supply of missing gene products (e.g., G and/or M) would be accomplished as described above.

B. Methods of Using Recombinant Rhabdoviruses

The recombinant Rhabdoviruses produced as described above can be used (1) to target cells infected with infectious agents (e.g., bacteria, parasites, or viruses); (2) to target diseased or abnormal cells; (3) to study the envelope proteins of other viruses for research purposes; (4) to treat a disease or infection and to remove abnormal cells; (5) to image specific cells or tissues for diagnostic purposes; and (6) to use as a kit for diagnoses and/or disease tracking.

(1) To Target Cells Infected with an Infectious Agent

Recombinant Rhabdoviruses which express a fusion protein can be further engineered to also express an attachment protein that recognizes a protein located on the surface of the cell that results from infection by some infectious agent (e.g., bacteria, viruses, or parasites). Such a to recombinant Rhabdovirus could be utilized to (1) diagnose the presence of the infectious agent by producing a reporter protein if infection by the recombinant virus occurs or (2) to treat the infection.

One contemplated example is a Rhabdovirus that expresses the CD4 protein in conjunction with the fusion protein. If using RV, both the CD4 and fusion proteins would be created from plasmids, where the genes encoding these proteins are fused to the gene encoding the tail of the G protein as described by Mebatsion et al., 1997. The absence of the tail of the G protein in RV constructs would prevent CD4 and fusion protein expression on the surface of the recombinant RV construct. If using VSV, the CD4 and the fusion proteins may be expressed alone without being fused to a portion of the G protein. The genes encoding the CD4 protein and the fusion protein would be placed downstream from the N and P genes, but before the L gene. The L gene is the last gene in these constructs. It is important that the ratios of the Rhabdovirus proteins remain substantially the same in all constructs for proper assembly to occur.

A VSV that expresses the F protein of paramyxovirus strain SV5 and CD4 would be capable of infecting both HIV-1 infected macrophages and T cells. Such a recombinant VSV can be further engineered to express a reporter protein upon entry into the HIV-1 infected cells. This construct is in contrast to those described by Schnell et al. (1997) and Mebatsion et al. (1997), which can only infect T-cells due to the presence of the co-receptor CXCR4. CD4/CXCR4 constructs attached only to HIV-1 infected T cells and not to HIV-1 infected macrophages.

For purposes of targeting cells in vitro (tissue culture cells or cells from a tissue sample, such as a biopsy), the isolated recombinant Rhabdovirus is incubated with the cells using techniques known in the art. Detection of infection by the recombinant Rhabdovirus could proceed by determining the presence of a reporter gene, such as a green fluorescent protein.

For purposes of targeting cells in vivo, the isolated recombinant Rhabdovirus could be administered by either intravascular (i.v.), intramuscular (i.m.), subcutaneous (s.c.), oral, or by any means in which the recombinant virus can be delivered to tissue (e.g., needle or catheter). Alternatively, the recombinant Rhabdovirus could be administered topically for insertion into epithelial cells. Another method of administration would be as an aspirate. The recombinant virus would be given sufficient time to circulate, attach, infect, and produce the reporter protein. Reporter protein should be detectable within 24 hours and certainly within 36 hours.

The viral agents infecting the cells to be targeted contemplated include members of the following virus families: Arenaviridae, Bunyaviridae, Coronaviridae, Filoviridae, Flaviviridae, Herpesviridae, Hepadnaviridae, Orthomyxoviridae, Paramyxoviridae, Poxviridae, Retroviridae, and Rhabdoviridae. Additional viral agents for targeting by recombinant Rhabdoviruses considered include: African Swine Fever Virus, Borna Disease Virus, Hepatitis X, HIV-1, Human T Lymphocyte virus type-1 (HTLV-1), HTLV-2, lentiviruses, Epstein-Barr Virus, papilloma viruses, herpes simplex viruses, hepatitis B and hepatitis C.

Proteins of bacterial agents capable of residing intracellularly in an infected host are also potential targets contemplated for infection by the recombinant Rhabdovirus. The intracellular bacteria contemplated include, amongst others: *Shigella flexneri, Salmonella typhi,* Legionella species, mycobacteria, and chlamydiae (See G. L. Mandell, "Introduction to Bacterial Disease" in Cecil Textbook of Medicine, (W. B. Saunders Co., 1996) 1556–7). These bacteria would be expected to express a bacteria-related protein on the surface of the infected cell to which the recombinant Rhabdovirus would attach.

Proteins of parasitic agents, which reside intracellularly, also are targets contemplated for infection by the recombinant Rhabdovirus. The intracellular parasites contemplated include, for example, Protozoa. Protozoa which infect cells include: parasites of the genus Plasmodium (e.g., *Plasmodium falciparum, P. Vivax, P. ovale* and *P. malariae*), *Trypanosoma cruzi,* Leishmania, and Cryptosporidium.

(2) Methods to Target Diseased Cells

Diseased and/or abnormal cells would be targeted using the recombinant Rhabdoviruses previously described by the same administration methods as previously described. The diseased or abnormal cells contemplated include: neoplastic cells, pre-neoplastic cells, benign tumors, or polyps, café au lait spots, leukoplakia and other skin moles.

The recombinant Rhabdoviruses will be targeted using an antireceptor that will recognize and bind to a receptor expressed on the diseased or abnormal cell. Fusion of the recombinant Rhabdovirus virion will be mediated by a fusion protein as previously described. Possible antireceptors used in the recombinant Rhabdovirus will include the natural antireceptor for any particular cell receptor.

Alternatively, recombinant Rhabdoviruses can be engineered to express an antibody or polypeptide fragment thereof, a bifunctional antibody, Fab, $F(ab')_2$, Fc, Fv, or single chain Fv (scFv) as their attachment protein. Such antibody fragments would be constructed to identify and bind to a specific receptor. These antibodies can be humanized, human, or chimeric antibodies (for discussion and additional references see S. L. Morrison "Antibody Molecules, Genetic Engineering of," in Molecular Biology and Biotechnology: A Comprehensive Desk Reference 1995; S. D. Gillies et al., (1990) *Hum. Antibod. Hybridomas* 1(1): 47–54; E. Harlow and D. Lane, Antibodies: A Laboratory Manual (1988) Cold Spring Harbor Press, NY). Expression of functional single chain antibodies on the surface of viruses has been reported using vaccinia virus (M. C. Galmiche et al., (1997) *J. Gen. Virol.* 78: 3019–3027). Similar methods would be utilized in creating a recombinant Rhabdovirus expressing a fusion protein and an antibody or antibody fragment. The genes of monoclonal antibodies that target, for example, tumor associated antigens (TAA) expressed on the cell surface (e.g. PMA or PSA), can be isolated and used to produce the desired recombinant Rhabdovirus, as would be known to an individual skilled in the art.

For example, the genes of antibodies which recognize TAAs can be fused to either the F Protein, the complete G protein or the G stem or expressed in combination with the F Protein and G protein or G stem. Examples of antibodies include those antibodies which react with malignant prostatic epithelium but not with benign prostate tissue (e.g., ATCC No. HB-9119; ATCC HB -9120; and ATCC No. HB-11430) or react with malignant breast cancer cells but not with normal breast tissue (e.g., ATCC No. HB-8691; ATCC No. HB-10807; and HB-108011). Other antibodies or fragments thereof which react with diseased tissue and not with normal tissue would be apparent to the skilled artisan.

(3) To Study the Envelope Proteins of Other Viruses

The envelope proteins of viruses that express a lipid membrane envelope can be studied using a recombinant Rhabdovirus. Such a recombinant virus would allow study of (1) the tropism of a particular virus envelope protein; and (2) the cell receptors targeted by the virus envelope protein (antireceptor). For certain hazardous viruses, experimentation can proceed without the usual need for high-level containment areas. The virus envelope proteins of interest in such study are those of the following virus families, for example: Arenaviridae, Bunyaviridae, Coronaviridae, Filoviridae, Flaviviridae, Herpesviridae, Hepadnaviridae, Orthomyxoyviridae, Paramyxoviridae, Poxviridae, Retroviridae, and Rhabdoviridae. Additional viruses with protein-expressing lipid envelopes include: African Swine Fever Virus, Borna Disease Virus and Hepatitis X. The hazardous viruses contemplated for study using recombinant Rhabdoviruses include amongst others: Ebola virus (subtypes Zaire, Reston and Sudan), Marburg Virus, Lassa Fever, Dengue, Hantaan virus, Korean hemorrhagic fever, Kyasanur Forest virus, Puumula virus, Seoul virus, Simian hemorrhagic fever virus, HIV, HTLV and South American hemorrhagic fever virus (B. N. Field' Virology volumes 1 and 2, New York, N.Y. 1996).

Production of Rhabdoviruses expressing the envelope proteins of other viruses would be accomplished by the same techniques as described above. Administration of the recombinant Rhabdoviruses to target cells would also be accomplished as previously described. Example 6 describes a recombinant VSV that expresses the envelope protein of Ebola virus, Reston strain.

(4) Methods of Treating a Disease or Infection Using Recombinant Rhabdoviruses

By "diseased cell" is meant a cell that is infected with a virus, bacteria or parasite, or a cell that is histologically or genetically aberrant for its tissue type. The recombinant Rhabdovirus particles described above can be used therapeutically to treat or ameliorate a condition resulting from a disease or an infection. If the diseased or abnormal cells are targeted and infected by a recombinant Rhabdovirus, and the M protein is expressed, the infected cell will eventually die as a result of M protein cytotoxicity. Recombinant VSV constructs that do not express a fusion protein have been demonstrated to kill and reduce the number of cells infected with HIV-1 for this reason (See Schnell et al., 1997).

Recombinant Rhabdoviruses that express antibodies or antibody fragments which recognize, for example, a specific tumor associated antigen (TAA) could target certain cancer cells that express at least one TAA (H. I. Scher et al., in V. T. DeVita et al., Cancer: Principles and Practice of Oncology (1996) 1300–1320). Potential TAAs that can serve as the target of modified Rhabdoviruses include: β-human chorionic gonadotrophic hormone (β-HCG) and α-fetoprotein (AFP) which are expressed in brain tumors; the products of BRCA1, BRCA2 and carcinoembryonic antigen (CEA), which are expressed in breast cancers; tyrosinase and the MART-1 antigens associated with melanomas; members of the c-erbB family; MUC1/REP expressed in breast cancer tissues; TuAg.1; and epidermal growth factor receptor (EGFR) which is expressed in lung cancers (V. T. DeVita et al., Cancer: Principles and Practice of Oncology (1996)). Such Rhabdovirus pseudotypes are contemplated for use in treating cancer by infecting individuals with a therapeutically effective amount of a recombinant Rhabdovirus that targets the cancer cells and after infection, lyses and kills the cancer cell. Other TAAs for expression on recombinant Rhabdovirus would be known to the skilled artisan.

The recombinant Rhabdoviruses of the present invention could be engineered to be capable of replicating in the targeted cell after entry and reinfecting other target cells. These recombinant Rhabdoviruses would be unable to infect healthy cells.

(5) A Method of Imaging Cells

For diagnosis, determining disease progression or regression, or to study whether a particular recombinant Rhabdovirus can infect a cell, a recombinant Rhabdovirus can be constructed to express a reporter protein or fluorescent protein. These reporter proteins would be transcribed and translated only if the recombinant Rhabdovirus successfully infects the cell. The presence or absence of the reporter protein will determine whether or not the recombinant Rhabdovirus can infect the cell. Alternatively, recombinant Rhabdoviruses that express a reporter protein could be used when studying the tropism of virus envelope proteins or even other protein-protein (e.g., receptor-ligand) interactions. Detection of a reporter protein would indicate the presence of a disease. Examples 5 and 7 describe representative recombinant Rhabdoviruses used to image cells.

(6) A Diagnostic Kit for Detecting Diseased Cells

As discussed above, a kit can be prepared that comprises a recombinant Rhabdovirus capable of infecting a diseased or abnormal cell that upon successful infection would produce a reporter protein. The recombinant Rhabdovirus would be prepared to recognize a cell receptor associated with a disease. For example, the attachment protein expressed by the recombinant Rhabdovirus could recognize a tumor associated antigen (TAA) and would be able to detect cancer or a particular type of cancer. These kits can be used in conjunction with existing histological staining techniques to determine more quickly, as well as more accurately, what disease is present. The kit could additionally be used to ascertain the stage of a disease (e.g., cancer stage I versus cancer stage IV). This would be useful for purposes of diagnosis and determining what therapy or therapies may be appropriate in treating a particular subject's disease.

The preferred kit would have the recombinant Rhabdovirus prepared for contact with the tissue sample from a biopsy, for example. The tissue sample or aspirated cells then would be cultured with the recombinant Rhabdovirus, as would be known in the art. After incubation with kit Rhabdovirus, the cells and/or tissue would be examined for the presence or absence of a reporter protein.

Kits could also be prepared as above for use in vivo. The pre-prepared, recombinant Rhabdoviruses could be administered to a subject via one of the previously discussed methods of administration. Expression of the reporter gene may be detected in skin cells or during a surgical procedure. For surgery, detection of diseased or abnormal cells versus healthy (or normal) cells would permit surgeons to determine how much diseased tissue needed to be resected by margins determined by examining reporter protein expression in cells infected by the Rhabdoviruses.

The following examples therefore, specifically point out preferred embodiments of the present invention, and are not to be construed as limiting in any way the remainder of the disclosure. Other generic configurations will be apparent to one skilled in the art.

C. EXAMPLES

Example 1

Creation of a Modified Rhabdovirus

Construction of Recombinant VSV cDNAs. A diagram of the method used, in this example, to construct a recombinant VSV that expresses the F protein of paramyxovirus SV5 is shown in FIG. 5. Full-length VSV cDNAs encoding G proteins with truncated cytoplasmic domains were generated by replacing the gene encoding the wild-type G protein in pVSVFL(+)$_{I/NJG}$ (N. Lawson et al., Proc. Nat'l Acad. Sci. USA (1995) 92: 4477–4481). Another version of CT-1 was also constructed, which contained three consecutive stop codons, and which had the remaining portion of the cytoplasmic tail coding region to the NheI site deleted. This mutant is called CT-1TS (CT-1 Triple Stop) and was generated using standard PCR-mediated mutagenesis methods with a sense-strand primer (MW-36) complementary to nucleotides 975–997 (see the sequence for the complete genome of VSV-Indiana, GenBank # J02428), which are 5' to the KpnI site in the G protein cDNA, and an antisense oligonucleotide (5'-TATATGCTAGCTTATTATTATCG GAGAACCAAGAATAGTCCAATG-3') (SEQ ID No: 2). The three stop codons that were introduced are indicated in boldface type, and the NheI site used for cloning is underlined.

A plasmid encoding the G protein deletion mutant (pVSV-ΔG) was generated by removing the MluI to NheI fragment from pVSVFL(+)-2 (Lawson et al., (1995) Proc. Nat'l Acad. Sci. USA 92: 4477–81), filling in with Klenow fragment, and subsequent re-legation of the plasmid. Therefore, pVSV-ΔG retained the transcriptional regulatory sequences and a portion of the 3' untranslated region of the G protein gene, however it lacked the open reading frame (ORF) of the G protein coding region. An oligonucleotide-derived polylinker region (5'-MluI-KpnI-XhoI-SmaI-EagI-SphI-NheI-3') was also introduced between the MluI and NheI sites to facilitate the insertion of heterologous genes into the G protein gene transcription unit. This plasmid (pVSV ΔG-PL) was used to produce the recombinant VSV cDNAs encoding either human CD4 (pVSV ΔG -CD4), or a chimeric CD4 protein in which the transmembrane and cytoplasmic domains of CD4 were replaced with the corresponding regions of the VSV G protein (ΔG-CD4G).

The construct HAGS (HA-tagged G-stem), which encoded a truncated version of VSV G protein, was generated by PCR-mediated mutagenesis using a primer that overlapped the MluI site in the 5' nontranslated region of the G protein gene of pVSVFL(+)-2 and an antisense oligonucleotide 5'-AGGATGTTCGAAAGCGTAATCTGGTAC ATCATACGGATACTT GCAATTCACCCCAATG-3' (SEQ ID No: 3), which overlapped the NspV site (underlined) at position 1,280 in the VSV G protein gene, and which fused sequences complimentary to a portion of the G protein signal peptide (in italics) to the HA epitope (in bold-face type) followed by the membrane-proximal "stem" region of the G protein ectodomain. A similar construct (G-stem), which did not contain the HA epitope, was also generated using the appropriate mutagenic primer.

Recovery and production of recombinant VSV. Infectious viruses encoding mutant G proteins were recovered from plasmids by infecting approximately 3×10⁶ BHK-21 cells with the vaccinia virus vTF7-3 (T. R. Fuerst et al., (1986) Proc. Nat'l Acad. Sci. USA 83: 8122–8126), which encodes T7 RNA polymerase. After 1 hr, the inoculum was removed and the cells were transfected with a DNA-liposome suspension composed of 5 μg of the appropriate pVSV-G mutant plasmid and 5 μg, 3 μg, 5 μg, and 1 μg of plasmids containing the wild-type G, N, P and L genes, respectively, from the Indiana serotype of VSV (VSV$_{Ind}$). Cell transfections were performed, as described previously (Whitt et al., (1991) Focus 13:8–12) using a suspension of liposomes composed of dimethyldioctadecyl ammonium bromide (DDAB) and L-α-dioleoylphosphatidylethanolamine (DOPE) at a weight ratio of 1:2.5, respectively (Rose et al., (1991) BioTechniques 10: 520–525) except the liposome transfection reagent was prepared by ethanol injection (Campbell, (1995) BioTechniques 18:1027–1032). The transfected cultures were incubated for 24 hr, and the supernatants were placed on 5×10⁶ fresh BHK cells. After 48 hr incubation, the supernatants were centrifuged at 1,250×g for 10 min and filtered through a 0.2μ pore size filter (Millex-GS, Millipore) to remove the vaccinia virus.

Recovery of VSV-ΔG, ΔG-CD4/G and ΔG-CD4 was performed as described for the CT mutants except the supernatants from the primary transfections were transferred directly to dishes containing 2×10⁶ BHK cells, which were pre-infected with vTF7-3 and transfected with 10 μg of the G protein expression plasmid pBS-G-φT. After a 24 hr incubation, the supernatants were collected, cells were fixed with 3% paraformaldehyde and then examined by indirect immunofluorescence using anti-M protein-specific (23H12) or N protein-specific (10G4) monoclonal antibodies (L. Lefrancois et al, Virology (1982) 121: 157–167). Supernatants from successful recoveries were used to infect BHK cells that transiently expressed the G protein in the presence of 1-β-D arabinofuranosylcytosine (AraC, 25 μg/ml). Working stocks of the G-complemented viruses were filtered through 0.2μ filters to remove the residual vaccinia virus and titers were determined by indirect immunofluorescence microscopy at 10 to 16 hr post-infection using the antibodies described above, or the anti-CD4 monoclonal antibody Sim.2 (D. E. McCallus et al., Viral Immuno. (1992) 5: 163–172) obtained from the NIH AIDS Research and Reference Reagent Program.

VSV-HAGS recovery using a VSV Minivirus. The recombinant VSV-HAGS was recovered by an alternative strategy in which a VSV minivirus (GMMG), which expresses only the VSV G and M proteins (E. A. Stillman et al., J. Virology (1995) 69: 2946–2953), was used to provide the source of complementing G protein. Approximately 10⁶ vTF7-3 infected cells were transfected with 10 μg of pVSV-HAGS and 3 μg, 5 μg, and 1 μg of plasmids encoding the wild-type VSV$_{Ind}$ N, P and L proteins, respectively. The transfection mix was removed after 3 hr, and the cells were then superinfected with GMMG particles at a m.o.i. of one. Fresh medium was added directly to the cells after absorbing the GMMG minivirus for 1 hr. Supernatants were harvested 18 hr later and then filtered to remove the vaccinia virus.

Example 2

In vitro Administration of Recombinant VSV Containing a Fusion Protein to Cells

The filtrate was then applied to cells in 10 cm dishes. After 18 to 24 hr, the cells were examined for cytopathic effects (CPE). Supernatants from cultures exhibiting CPE were titered, and individual plaques were purified. Plaque purified isolates were used to infect BHK cells at a m.o.i. of one for the production of stocks of the tail mutant viruses. Direct sequencing of viral RNA isolated from each of the mutants was performed to ascertain whether the recovered virus contained the appropriate mutations.

One-half of each filtered supernatant from the VSV-HAGS/minivirus technique was used to infect fresh cells. Successful recoveries were indicated when cultures showed the typical cytopathic effects indicative of a normal VSV infection 18 to 24 hr post infection. The supernatants from those cultures were then titered and stocks of the co-complementing viruses were produced by infecting fresh cells at a m.o.i. of 0.01. Supernatants, which contained both VSV-HAGS and GMMG, were harvested after 24 hr, and the VSV-HAGS and GMMG particles were concentrated by centrifugation and then separated by banding using 20%–45% sucrose gradients. The lower fraction, which usually contained approximately 300-fold more VSV-HAGS than GMMG, was recovered by side-puncture and the amount of VSV-HAGS to GMMG was determined by an immunofluorescence-based titering assay utilizing either an N protein-specific (for VSV-HAGS) or a G protein-specific monoclonal antibody. To obtain a stock of VSV-HAGS, which was free of GMMG, the partially purified VSV-HAGS was completed by expressing the G protein from the New Jersey serotype of VSV (G$_{NJ}$). Then, neutralizing antibody, which was specific for the Indiana serotype of VSV (VSV$_{Ind}$), was added to the culture medium. The amount of Indiana-specific sera used completely neutralized all virus produced by the VSV-HAGS/GMMG coinfected cells. After three consecutive passages on cells expressing G$_{NJ}$ and in the presence of anti-VSV$_{Ind}$ neutralizing antibody, the titers of VSV-HAGS reached approximately $10^8$ IU/ml, while 0.5 ml of the supernatant contained no detectable GMMG. High titer stocks of pure VSV-HAGS complemented with the VSV G$_{Ind}$ protein were then made as described above for VSVΔG.

Example 3
Administration of Modified VSV to Cells in vivo

Recombinant VSV particles prepared by either of the methods described above are inoculated into a subject infected with HIV-1. The concentration of the virus to be administered to a subject may vary, but the titer of the virus to be administered preferably should be in the order of about $10^6$ to $10^{12}$ IU/ml. The amount of the virus used may be greater if the patient has a relatively high number of infected cells. The viruses harvested as described in Example 1 would be resuspended in an appropriate carrier or excipient for purposes of injection.

Example 4
Analysis of Infectivity of Recombinant VSV Expressing Paramyxovirus SV5 F Protein and the Envelope Protein of Ebola Virus Plasmids. Full-length cDNAs encoding the Ebola Reston virus glycoprotein (ResGP) (A. Sanchez et al., (1996) *Proc. Nat'l Acad. Sci. USA* 93: 3602–3607), VSV G protein (J. K. Rose et al., (1982) *Cell* 30: 753–762), and influenza A/turkey/Ireland/1378/83 (H. Niwa et al., (1991) *Gene* 108: 193–200) are designated pCResGP, pCVSVG, and pCTH, respectively.

Cells. Vero, BHK, MDCK and MDBK cells were grown in Eagle's minimal essential medium (MEM) supplemented with 10% fetal calf serum (FCS), L-glutamine (Gibco), vitamin and amino acid solution (Gibco), and penicillin-streptomycin solution (Sigma). For L-cells, horse serum was used instead of FCS. 293T, COS-1, NIH-3T3 and Tb1Lu cells were cultured in high-glucose Dulbecco's modified Eagle's medium containing 10% FCS, L-glutamine, and the antibiotics. CHO clone 22 cells, provided by Dr. E. Ruley (Vanderbilt University), were cultured in Ham's F-12 medium containing 5% FCS, L-glutamine, and antibiotics. DBT cells, a murine astrocytoma cell line provided by Dr. S. Makino (University of Texas), were grown in MEM supplemented with 10% newborn calf serum, tryptose-phosphate broth (Gibco) and antibiotics. Clone C6/36 cells, from a mosquito larvae cell line, were grown in MEM supplemented with Earl's BSS, non-essential amino acids, L-glutamine and 10% FCS.

Generation of recombinant VSV. The coding region of the G protein gene in a full-length cDNA clone of the VSV genome (Indiana serotype, VSV$_{Ind}$) (N. D. Lawson et al., 1995) was replaced with the coding region of a modified version of the green fluorescent protein (GFP) gene (M. Chalfie et al., (1994) *Science* 263: 802–5), in which serine 65 was replaced with a threonine. This plasmid was designated pVSV-ΔG*. BHK cells in 60 mm dishes were infected at a multiplicity of 10 with the recombinant vaccinia virus vTF7-3 (T. R. Fuerst et al., 1986), which encodes bacteriophage T7 RNA polymerase, for 1 hr at 37° C. The infected cells were then cotransfected with pVSV-ΔG*, the VSV nucleocapsid protein (N), phosphoprotein-(P), polymerase protein-(L), and glycoprotein (G)-expressing plasmids at weight ratios of 10, 3, 5, 1 and 3 μg respectively as indicated previously (E. A. Stillman et al., (1 995) *J. Virology* 69: 2946–2953). The transfection ratio used approximately emulated the transcription and translation ratio observed in naturally replicating VSV.

The supernatant fluid was harvested at 48 hr post transfection, and one half of the supernatant was used to infect a second plate of cells that had been infected with vTF7-3 and transfected with 5 μg of plasmid encoding the G protein only. Cells were examined for GFP expression at 24 hr post infection by fluorescence microscopy. The presence of fluorescent cells indicated that VSV genome had been successfully recovered. Additional passages of supernatant containing VSVΔG* complemented with G protein (VSVΔG*-G) through cells expressing the G protein from plasmid DNA in the presence of 25 μg/ml of cytosine-β-D-arabinofuranoside were performed to obtain high titer stocks of VSVΔG*-G. The virus stocks were filtered through a membrane with a 0.2 μM pore to remove the vaccinia virus. Virus titer in the supernatant fluid was then determined again by infecting BHK cells and quantifying the number of cells expressing GFP by fluorescence microscopy.

Preparation of VSVΔG* Complemented with YSV G or ResGP or Without Complementation. 293T cells were transfected with pCVSVG, pCResGP or pCAGGS using Lipofectamine (Gibco). Thirty-six hours after transfection, cells were infected with the VSVΔG*-G described above, at a multiplicity of infection (m.o.i.) of about one for one hour at 37° C. They were then washed with PBS three times, and medium was added. After 24 hours of incubation at 37° C. in a $CO_2$ incubator, culture fluid was collected and centrifuged to remove cells. Each virus stock was stored at −80° C. until used.

Titration of recombinant VSVs complemented with receptor-binding proteins in different cell lines. Cell monolayers were grown on cover slips, washed with PBS and then infected with serially diluted virus stocks. After 1 hour of absorption at 37° C., the inoculum was aspirated and growth medium was added. The cells were incubated at 37° C. for 12–14 hours in a $CO_2$ incubator, washed with PBS, fixed with 10% formalin in PBS. Infectious units of recombinant VSV in different cell lines were determined by counting the number of green fluorescent protein (GFP) expressing cells.

Example 5
Method of Determining Tropism of VSV-Ebola Reston Pseudotype and Analysis of Cells So Infected This example is from A. Takada et al., "A novel system for functional analysis of Ebola Reston virus glycoprotein," (in press 1997) *Proc. Nat'l Acad. Sci. USA*. Determination of cell tropism using the recombinant VSV virus particles prepared as described above is as follows. Cell monolayers were grown on cover slips, washed with phosphate buffered saline (PBS) and then infected with serially diluted virus stocks. After 1 hour of absorption at 37° C., the inoculum was aspirated and growth medium was added. The cells were incubated at 37° C. for 12–14 hours in a $CO_2$ incubator, washed with PBS, and fixed with 10% formalin in PBS. The infectious units of the recombinant virus expressed in different cell lines were determined by counting the number of green fluorescent protein (GFP) expressing cells. See FIG. 4 for an example of the cells successfully infected by the recombinant VSV constructs: VSVΔG*-G, VSVΔG*-ResGP and VSVΔG*. The infectivities of these recombinant VSV constructs are presented in Table I.

TABLE I

Infectivities of recombinant VSVs for different cell lines[a]

| Cell Line (species) | Infectious Unit ($\log_{10}$/0.1 ml) | | |
|---|---|---|---|
| | VSVΔG*-G | VSVΔG*-ResGP | VSVΔG* |
| Vero (monkey) | 6.7 | 5.2 | 2.1 |
| COS-1 (monkey) | 6.3 | 5.1 | 2.1 |
| 293T (human) | 6.5 | 5.1 | 2.0 |
| BHK (hamster) | 6.7 | 3.4 | 2.4 |
| CHO (hamster) | 5.7 | 3.7 | 2.1 |
| L (mouse) | 6.1 | 33.6 | 1.8 |
| NIH3T3 (mouse) | 5.0 | 3.3 | 1.0 |
| DBT (mouse) | 6.6 | 3.7 | 2.5 |
| MDCK (dog) | 6.2 | 3.9 | 1.8 |
| MDBK (cow) | 5.2 | 2.6 | 0.8 |
| CEF (chicken) | 6.4 | 3.5 | 2.2 |
| Tb1Lu (bat) | 5.1 | 2.9 | 0.3 |
| C6/36 (mosquito) | 3.3 | 0.6 | 0.3 |

[a]Cells from a given line were infected with viruses from the same batch prepared as described in Example 4. The data are representative results from experiments repeated with three different batches of viruses. Twelve to fourteen hours after infection, infectious units of the recombinant virus expressed in different cells were determined by counting the number of GFP-expressing cells.

Results. In contrast to VSVΔG*-G, the infectivity of VSVΔG*-ResGP virus stock was greatly dependent on the type of cell line. With cells originating from primates (e.g., Vero, 293T and COS-1), infectivity titers of VSVΔG*-ResGP were 100-fold higher than those with cells from hamsters, dogs, cattle, mice, chickens or bats. VSVΔG*-ResGP did not infect the C6/36 insect cells. These results suggest that key determinants of Ebola virus entry into cells (e.g., specific tropic characteristics of the antireceptor) differ among animal species.

Incorporation of ResGP into recombinant VSV particles. Viral proteins were also analyzed by 10% SDS-PAGE under reducing conditions. FIG. 3 shows lysates of 293T cells, which were transfected with an expression vector plasmid containing the VSV G gene (lane 1), the ResGP gene (lane 2), or the vector plasmid only (lane 3). The 293T cells were labeled for 5 hours with [$^{35}$S]-methionine 30 hr post transfection with the recombinant virus. Proteins in cell lysates were precipitated using a monoclonal antibody specific to the VSV G protein (FIG. 3, lane 1) or ResGP (lanes 2 and 3). Recombinant VSVs, including VSVΔG* complemented with VSV G protein (lane 4; VSVΔG*-G), ResGP (lane 5; VSV ΔG*-ResGP) or lacking complementation (lane 6; VSV ΔG*), were labeled with [$^{35}$S]-methionine and purified by differential centrifugation and sedimentation through 25–45% sucrose gradients.

Example 6
Time Course Analysis of Green Fluorescent Protein (GFP) Expression in Cells Infected by a Recombinant VSV Recovery of infectious virus from plasmids. Recovery of infectious particles is accomplished by infecting $10^6$ BHK-21 cells with vTF7-3 vaccinia for 60 minutes and then transfecting the cells with 10 μg of plasmid encoding the various full-length VSV constructs and 3 μg, 5 μg, and 1 μg of plasmids encoding the VSVInd nucleocapsid protein (N), phosphoprotein (P) and polymerase (L), respectively. Cells were incubated for two days to allow replication and assembly of viral particles. The supernatant from the cells was then plated directly onto fresh BHK cells, and the cells were incubated for 24 hours to permit virus amplification. The supernatants from these cultures were then passed through the filter as described above. The filtrate was transferred onto fresh BHK-21 cells. Following the hour absorption, the supernatant was replaced with DMEM containing FCS. The media of cultures exhibiting CPE of a VSV infection were then removed and the virus was plaque purified. Virus stocks were subsequently prepared by infection, for example, of $10^7$ cells with approximately $10^5$ plaque forming units (p.f.u.) of the plaque isolate. The supernatant from these cultures was then used for all subsequent infections. Direct sequencing of the viral RNA isolated from every recovered virus is performed to ensure that the recovered virus was derived from a plasmid.

Time course for GFP expression in ΔG-GFP infected cells. BHK-21 cells were infected with ΔG-GFP particles pseudotyped with VSV G protein in trans. The cells were examined for GFP expression using fluorescence microscopy at the times indicated. Phase contrast images of the same fields were also collected and are shown in the right-hand panels of FIG. 6.

Example 7
Method of Treating Individuals Infected with a Virus, Bacteria or a Parasite A subject is treated using a recombinant Rhabdovirus that has been engineered, as discussed above, to target cells infected with either a virus, parasite or bacterium that leads to the incorporation on the cell surface of a protein derived from the infectious agent. This protein acts as a receptor that is to be targeted by the recombinant antireceptor of the recombinant Rhabdovirus agent.

One example would be the treatment of a subject infected with HIV-1. The CD4 protein would be expressed on the surface of the recombinant Rhabdovirus along with a heterologous fusion protein. The recombinant Rhabdovirus has the ability to recognize, bind to and infect a cell which expresses the mature HIV-1 envelope protein, gp120. The recombinant Rhabdovirus would contain a polycistronic nucleic acid that comprises the gene encoding the M protein. This Rhabdovirus would be capable of lysing the cells that it infects. As a result, the number of infected HIV-1 cells, such as macrophages and T cells, could be reduced in number, and the virus thereby kept in check. The amount of recombinant Rhabdovirus administered would be approximately similar to what is administered when using most gene therapy vectors.

Example 8
Method of Treating Subjects with Cancer

A recombinant VSV is prepared as described above except that the recombinant expresses an attachment protein (antireceptor) that can identify a protein associated with some forms of cancer, such as CEA, prostate specific antigen (PSA) or PMA.

Example 9
Creation of a Recombinant Rhabdovirus Containing a Polypeptide Fragment of a Fusion Protein A recombinant Rhabdovirus, such as VSV, is constructed to express a fusion protein, such as the SV5 F protein, or a fragment of the fusion protein joined to the stem region of VSV G protein encompassing the putative oligomerization domain of G protein, the transmembrane domain and the cytoplasmic tail of G protein. These constructs would be used to infect cells and then the infectivity of the resulting virus would be compared on various cells lines.

Example 10
A Method of Identifying Fusion Proteins Using Only cDNAs

A recombinant Rhabdovirus, such as VSV, is constructed to express an attachment protein and a fusion protein candidate. The attachment protein could be CD4 and the cells targeted could be cells expressing the HIV-1 envelope protein gp 120/gp160. The construct expressing the candidate fusion protein would be compared to constructs that express the fusion protein of Paramyxovirus SV5 and CD4 (a positive control), and VSV constructs that express CD4 and the VSV G protein only. The degree of infectivity by these constructs could be compared using a reporter protein, such as the green fluorescent protein used above and as described in Examples 5 and 6.

The constructs could be prepared using any of the methods described in the specification.

Example 11
Infectivity of Recombinant CD4-VSV Pseudotyped with the SV5 F Protein on Cells Expressing HIV gp160

Pseudotyping CD4-VSV with Paramyxovirus SV5 F proteins. BHK-21 cells expressing the SV5 F protein (using the vaccinia T7 expression system) were infected with CD4-VSV that had been previously pseudotyped with wild-type VSV G protein. The supernatant was harvested 18 hr post-infection and then filtered to remove the vaccinia virus. The resulting supernatant contained recombinant VSV that had both CD4 and SV5 protein in the viral envelope, but that lacked VSV G protein. Residual infectivity from the inoculum (e.g., from the G protein pseudotyped CD4 virus) was eliminated by addition of neutralizing antibody specific for VSV G protein.

Infectivity of recombinant CD4-VSV pseudotyped with the SV5 F protein on cells expressing HIV gp160. BHK-21 cells were infected with a recombinant vaccinia virus expressing T7 RNA polymerase and transfected with varying amounts of an expression plasmid encoding the HIV gp160 protein. After 10 hr, which allowed accumulation of gp120-gp41 on the cell surface, the cells were infected with CD4/F-VSV. All plates were infected with the same amount of CD4/F virus inoculum. Cells were incubated for an additional 6 hrs to allow expression of VSV-specific proteins and then examined for expression of the VSV N protein by immunofluorescence microscopy. The number of infected cells per plate was determined by counting cells that were immunoreactive for the VSV N protein. FIG. 7 demonstrates that in cells transfected with increasing amounts of plasmid encoding gp160, there is a corresponding increase in the number of cells that become infected with the CD4-SV5 F pseudotyped ΔG VSV.

Example 12
Generation of Recombinant VSV Encoding a PSA-specific ScFv for Targeting Prostate Cancer Construction of ScFv-GS. First, the V-H and V-L domains from a hybridoma cell line that produces antibodies to prostate-specific antigen (PSA), or other tumor-specific antigens, are cloned using standard methods for ScFv construction. Briefly, sequences for the variable domains are obtained following RT-PCR amplification of poly-A containing mRNA isolated from the appropriate hybridoma cells. The poly-A RNA is used as the template for the reverse transcription (RT) reaction, and the primers that are used are similar to those described previously (R. Orlandi et al., (1989) *Proc. Natl. Acad. Sci. USA*, 86: 3833–3837.). The amplified V domains are cloned into pBluescript, and the sequence of the amplified regions are determined by standard methods. The sequences are analyzed for open reading frames and will be compared to known $V_H$ (variable heavy chain) and $V_L$ (variable light chain) sequences. Once the sequences are confirmed, these clones are used to construct the ScFv gene. The sequences encoding the $V_H$ and $V_L$ domains are joined using an oligonucleotide linker. The linker encodes a short Gly-Ser peptide that connects the C-terminus of the first V region and the N-terminus of the second V (variable) region into a $V_L$-(Gly-Ser)-$V_H$ polypeptide. The intact ScFv gene is then joined to sequences encoding the VSV G protein signal sequence, such that following expression in eukaryotic cells, the protein is targeted to the endoplasmic reticulum and secreted. Expression analysis is used to confirm that the ScFv is functional and is able to bind the appropriate antigen (e.g., PSA).

Next the ScFv coding region is joined to sequences encoding the membrane-anchored stem region of a VSV G protein. A unique restriction site introduced into the G stem sequence is used to join the two coding regions such that the reading frame remains intact. The resulting molecule consists of the ScFv domain fused to amino acid E422 of VSV G stem (ScFv-GS). Expression analysis is used to confirm that the molecule is expressed and is localized to the plasma membrane of the transfected cells.

Lastly, the ScFv-GS gene is cloned into the multiple cloning site of pVSV-G-F such that the gene is under the transcriptional control of VSV. The resulting construct is called pVSV-ScFv-F. Recombinant ScFv-F virus is recovered from the plasmid pVSV-ScFv-F using standard procedures. Pure VSV-ScFv-F is generated following passage in cells not expressing wild-type VSV G protein.

Targeting of tumor cells expressing PSA. The cell line LNCaP is a model cell line for prostate cancer. These cells are known to express PSA and should serve as a target for recombinant ScFv-F virus. LNCaP cells are grown under standard culture conditions and then supernatants containing recombinant ScFv-F virus are added. Because the cells are lightly adherent and the monolayers are easily disrupted, the inoculum is not removed. Infection is assessed at 15 hours post-inoculation using a typical immunofluorescence-based infectious center assay. Controls include infection with wild-type recombinant VSV, the non-infectious mutant VSV-HAGS, which contains only the membrane-anchored G stem, and a recombinant that encodes only the ScFv-GS polypeptide without the fusion (F) protein. Specificity is determined by assessing the infectivity of ScFv-F virus on normal cells that do not express PSA.

Similarly, these constructs can be analyzed in animal models used for the study of prostate cancer. Mouse model systems for human prostate cancer have been developed and these should be ideal for the studies described. Pure recombinant VSV-ScFv-F is administered to animals bearing human prostate-specific tumors. The animals are monitored for several weeks to determine if there are any adverse effects resulting from administration of the recombinant virus. Animals are sacrificed and the tumor masses examined for changes in size, weight, vascularization and metastasis. Controls include infection with VSV-HAGS, which serves as the negative control. An additional control is the administration of a recombinant VSV-ScFv-GS that does not contain a fusion (F) protein. Like VSV-HAGS, this virus should be noninfectious. The VSV-HAGS construct allows the evaluation of effects associated with administration of a virus having the ScFv-GS polypeptide on the viral envelope.

Example 13
Infectivity of VSV-CD4 Recombinants

To study Infectivity of VSV-CD4 Recombinants, BHK-21 cells were infected with wild-type G protein pseudotyped recombinant ΔG-VSV encoding either CD4-G, CD4-GS, or both CD4-G and HAGS viruses. The pseudotyped viruses were absorbed for 60 min, the inoculum was removed, and then cell monolayers were washed extensively to remove any residual inoculum. Following infection, the cells were incubated in medium containing 5% FCS for 16 hours. After incubation, the medium, which contained pure recombinant VSV/CD4-G, CD4GS, or a mixture of CD4-G and HAGS viruses, was collected, and detached cells were removed by centrifugation at 2,500 rpm for 10 min. Aliquots of the supernatant were used to infect cells expressing the HXB subtype of the HIV-1 envelope protein. The supernatants were absorbed for 60 min in serum-free medium; the inoculum was removed and then replaced with serum-free medium. Infectivity was assayed by examining the number of cells expressing the VSV nucleocapsid protein by immunofluorescence microscopy.

100 µl of the VSV/CD4-G supernatant was used for the infectivity assay, whereas only 10 µl of the CD4-GS or CD4G+HAGS supernatants were used. A total of 60 VSV/CD4-G infected cells were found on the entire dish. This result corresponds to a titer of 600 infectious units per ml (IU/mi). In contrast, the titer of CD4-GS or CD4-G+HAGS was >$10^8$ IU/ml.

Results. The data shown in FIG. 8 demonstrates that virus containing CD4-G, but lacking a human chemokine coreceptor in the viral envelope, has extremely low infectivity on cells expressing the T-tropic HIV-1 envelope protein (HXB). In contrast, virus encoding CD4-GS (the CD4 ectodomain joined to amino acid E422 of the VSV G protein ectodomain, e.g., the "G stem") has very high specific infectivity. The specific infectivity of CD4-GS is nearly equivalent to the specific infectivity observed with wild-type VSV for its wild-type host cell target. Moreover, infection of HIV-1 envelope expressing cells by VSV/CD4-GS does not require a chemokine coreceptor. Analysis of purified VSV/CD4-GS virions has revealed that a proportion (~50%) of CD4-GS is cleaved at, or near the CD4/G-stem junction. This cleavage, which occurs during transport of the protein to the plasma membrane in infected cells, results in the release of virus particles that have both the membrane-anchored cleavage product (the G-stem) as well as full-length CD4-GS molecules (FIG. 9). Cleavage does not occur with CD4-G and consequently, the VSV envelope consists solely of CD4-G.

To determine if the G-stem (in this case an HA-epitope tagged version called HAGS) can enhance infectivity of virions, containing CD4-G, cells were coinfected with viruses encoding either CD4-G or HAGS separately. The virions produced from these cells contained both CD4-G and HAGS in the envelope. Infectivity of the CD4-G/HAGS virus was virtually identical to that of the CD4-GS. These results indicate that the VSV G-stem can enhance the infectivity of virus particles when incorporated into the viral envelope with a heterologous binding protein, in this case CD4-G. Other heterologous binding protein candidates would be readily known to the skilled artisan.

Example 14
VSV Recombinants Containing G-Stem: Infectivity and Model

Virus production and G-stem incorporation. Virus was produced as described in the experiment demonstrated in FIG. 8. The supernatant was harvested at 16 hours post-infection. Virions were concentrated by ultracentrifugation, and the amount of virus and the protein content of the virions were determined using SDS-PAGE. Virions proteins were visualized by staining with Coomassie blue or by Western blot analysis using an antibody specific for the cytoplasmic domain of VSV G protein (see FIG. 9).

Results. VSV/CD4-G infected cells produce approximately the same amount of virus as ΔG-VSV. This corresponds to ~10-fold less virus than wild-type VSV. In contrast, VSV/CD4-GS produces nearly wild-type amounts of virus (~70-75% of wild-type). Immunoblot analysis (FIG. 9) of equivalent amounts of CD4-G and CD4-GS virus, with an antibody which recognizes and binds to the last 15 amino acids of the VSV-G cytoplasmicdomain, shows that CD4-GS is cleaved and the corresponding the G-stem fragment is incorporated into recombinant VSV virions together with the full-length CD4-GS molecule.

Infectivity of VSV/CD4-GS produced from various cell types on cells. Virus was produced in the indicated cell types essentially as described in the experiment of FIG. 8. Supernatants were harvested at various times post-infection, which was dictated by differences in the susceptibility of the different cell types to lysis by VSV. A portion of the supernatant was used for the infectivity assays, and the remainder was subjected to ultracentrifugation to pellet virions. The amount of virus produced by each of the cell types was determined by densitometry of Coomassie blue stained gels following SDS-PAGE separation of the proteins. The relative infectivity displayed in FIG. 10 represents the amount of infectivity after normalization to viral protein pelleted from the supernatant. The relative infectivity does not correspond to IU/ml.

TABLE II

INFECTIVITY OF BSV/CD4-Q427 FOR X4 AND R5 SPECIFIC ENVELOPES

| HIV Isolate Designation Envelope Type | Virus Tropism | Vaccinia Vector | Infectivity* |
|---|---|---|---|
| None | — | vTF7-3 | − |
| JR-FL | M-tropic (R5) | vCB-28 | ++ |
| SF162 | M-tropic (R5) | vCB-32 | +++ |
| ADA | M-tropic (R5) | vCB-39 | ++++ |
| LAI IIIB (BH8; uncleaved) | T-tropic (X4) | vCB-16 | − |
| SF2 | T-tropic (X4) | vCB-34 | ++ |
| RF | T-tropic (X4) | vCB-36 | − |
| LAI IIIB (BH10) | T-tropic (X4) | vCB-40 | ++ |
| LAV | T-tropic (X4) | vCB-41 | + |

*"++++" = $10^6$–$10^5$ IU/ml;
"+++" = $10^5$–$10^4$ IU/ml;
"++" = $10^4$–$10^3$ IU/ml;
"+" = $10^3$–$10^2$ IU/ml;
"−" = <$10^2$ IU/ml (fewer than 10 infected cells per dish).

To assess the infectivity of the VSV/CD4-Q427 construct for X4 (T cell tropic envelope) and R5 specific envelopes (macrophage tropic envelopes), BHK-21 cells were infected with wild-type G protein pseudotyped recombinant G-VSV encoding CD4-GS fused at Q427 of the 511 amino acid G protein. The pseudotyped virus was absorbed for 60 min, the inoculum was removed, and then the cell monolayer was washed extensively to remove any residual inoculum. The infected cultures were subsequently incubated in medium containing 5% FCS for 16 hours. After incubation, the medium from the infected cultures, which contained pure recombinant VSV/CD4-GS(Q427) virus, was collected and detached cells were removed by centrifugation at 2,500 rpm for 10 min. A 100 µl aliquot of the supernatant was used to infect HeLa cells expressing the indicated HIV-1 envelope proteins as follows. The HIV-1 envelope proteins were expressed using vaccinia virus vectors which were supplied from the NIH AIDS Research and Reference Reagent Program. For expression, HeLa cells were infected with the indicated vaccinia virus vector by absorption for 60 min in serum-free medium. The inoculum was removed and replaced with medium containing 5% FCS, and 100 µg/ml AraC. The cells were incubated for 30 min, then 100 µl of the VSV/CD4-GS(Q427) supernatant was added directly to the medium, and the cultures were incubated for 4 hours to allow expression of the HIV-1 envelope and absorption of the CD4-GS(Q427) virus. After 4 hours, the medium containing the inoculum was removed and replaced with medium containing serum and AraC. The cultures were incubated for an additional 10 hours, and then the cells were fixed with 3% paraformaldehyde. Infectivity was assayed by examining the number of cells expressing the VSV nucleocapsid (N) protein using an N-specific monoclonal antibody and detection by immunofluorescence microscopy.

The data in Table II show that VSV/CD4-GS can infect cells expressing both T- and M-tropic HIV-1 envelope proteins. This infectivity occurs in a chemokine coreceptor-independent manner, since the recombinant virus was produced in a hamster cell line (BHK-2 1), which does not express a human chemokine coreceptor. Infectivity is absolutely dependent on expression of the HIV-1 envelope protein. Cells infected with either a recombinant vaccinia virus encoding T7 RNA polymerase (vTF7-3) or normal HeLa cells (not infected with vaccinia virus, but which were grown in the presence of AraC) were not susceptible to VSV/CD4-GS infection. In addition, infectivity requires a functional HIV-1 envelope protein (e.g., gp120-gp41), since cells expressing the uncleaved (e.g., gp160), fusion-defective mutant of LAI IIIB (expressed from vCB-16) were not susceptible for infection, even though this protein is expressed on the cell surface (data not shown). Vaccinia vectors are as described in C. C. Broder et al., (1995) *Proc. Nat'l Acad. Sci. USA* 92: 9004–9008.

The truncated version of the VSV G protein consists of the membrane-proximal 42 amino acids of the G protein ectodomain, the 20 amino acid transmembrane domain and the 29 amino acid cytoplasmic tail. The protein is generated from a precursor that contains the VSV-G protein signal sequence which is cleaved by signal peptidase following cotranslational insertion into the endoplasmic reticulum. The "maximum-length" stem that we have analyzed has 59 amino acids of the membrane-proximal ectodomain and the shortest version (which shows enhancement of fusion activity) has 29 amino acids of the ectodomain.

The membrane-anchored G stem appears to enhance the fusion activity of a variety of heterologous viral fusion proteins. This includes the fusion activity of HIV-1 gp120-gp41 from both T- and M-tropic viruses, the F protein of the paramyxovirus SV5, and the New Jersey serotype glycoprotein of VSV. We postulate that the stem somehow stabilizes, thereby enhancing, the fusion pores formed by these fusion proteins. The presence of the fusion pores usually necessitates the presence of another cofactor to manifest the full fusion activity of these proteins. In the case of HIV-1 envelope proteins, the cofactor is the chemokine coreceptors, for the paramyxovirus F proteins it is their cognate HN proteins, and for VSV G protein it is activation by acidic pH.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference in their entirety. This application also claims priority to U.S. Provisional Application Serial No. 60/068,472, filed Dec. 22, 1997, which is hereby incorporated by reference in its entirety.

What is claimed is:

1. A genetically engineered Rhabdovirus comprising: a heterologous fusion protein, that is effective to facilitate fusion of the Rhabdovirus to a target cell membrane; a heterologous G stem polypeptide; the Rhabdovirus N, P and L proteins; and a deletion of the nucleic acid sequence which encodes G protein of the Rhabdovirus.

2. The genetically engineered Rhabdovirus of claim 1, further comprising the Rhabdovirus M protein.

3. The recombinant Rhabdovirus of claim 1 or 2, wherein the fusion protein is from a Paramyxovirus simian virus 5 (SV5).

4. The genetically engineered Rhabdovirus of claim 1, further comprising an antireceptor protein, wherein said antireceptor is an antibody or CD4.

5. The recombinant Rhabdovirus of claim 4, wherein the G stem polypeptide and the antireceptor protein are expressed from a chimeric cDNA.

6. The recombinant Rhabdovirus of claim 1, wherein the G Stem polypeptide is a VSV G stem polypeptide.

7. The recombinant Rhabdovirus of claim 6, wherein the VSV G stem polypeptide comprises a $VSV_{Ind}$ polypeptide fragment starting from any residue between $^{404}$Gly and $^{440}$Phe and continuing to about residue $^{511}$Arg.

8. A method of producing a recombinant Rhabdovirus comprising an F Protein effective to facilitate fusion of the Rhabdovirus to a cell membrane thereof and a heterologous G stem protein comprising the steps of: (A) inserting a cDNA encoding Rhabdovirus N, P, L and G proteins into a suitable cell; (B) inserting a polycistronic cDNA copy of the Rhabdovirus genome containing at least the 3' and 5' Rhabdovirus leader and trailer regions containing the cis acting signals for Rhabdovirus replication, the genes encoding the N, P, M, and L Rhabdovirus proteins and a gene encoding an F Protein, wherein the nucleic acid sequence which encodes G protein of the Rhabdovirus is deleted and a heterologous G stem protein into the suitable cell; (C) culturing the cell under conditions that permit production of the recombinant Rhabdovirus; and (D) isolating said recombinant Rhabdovirus.

9. The method of claim 8, wherein the polycistronic cDNA further comprises a gene encoding an antireceptor protein or a polypeptide fragment thereof effective to target the recombinant Rhabdovirus to a cell.

10. The method of claim 9, wherein the antireceptor protein is selected from the group consisting of CD4, and an antibody or antibody fragment which recognizes a TAA expressed on a cell membrane.

11. The method of claim 8, wherein the polycistronic cDNA further comprises a gene encoding a G stem polypeptide.

12. The method of claim 8, wherein the recombinant Rhabdovirus is VSV.

13. The method of claim 8, wherein the F Protein is the Paramyxovirus strain SV5 F protein.

14. The method of any of claim 8 or 9, wherein the polycistronic cDNA or minivirus further comprises a cDNA encoding an antireceptor protein, wherein said antireceptor is an antibody or CD4.

15. The method of any of claim 8 or 9, wherein the polycistronic cDNA or minivirus further comprises a cDNA encoding a reporter protein.

16. A method of producing a recombinant Rhabdovirus which expresses an F Protein thereof effective to facilitate fusion of the Rhabdovirus to a cell membrane comprising the steps of:

(A) inserting into suitable cells a polycistronic cDNA comprising at least the 3' and 5' Rhabdovirus leader and trailer regions containing the cis acting signals for Rhabdovirus replication, the genes encoding the Rhabdovirus N, P, and L proteins and a gene encoding an F Protein;

(B) infecting the cells with a minivirus comprising the cis acting signals for Rhabdovirus replication and genes encoding the Rhabdovirus M protein and a heterologous G stem polypeptide, wherein the nucleic acid sequence which encodes G protein of the Rhabdovirus is deleted;

(C) culturing the cells under conditions to permit expression of the cDNA to produce the recombinant Rhabdovirus; and (D) isolating said recombinant Rhabdovirus.

17. The method of claim 16, wherein the recombinant Rhabdovirus is VSV.

18. The method of claim 17, wherein the F Protein is Paramyxovirus strain SV5 F protein.

19. A recombinant Rhabdovirus comprising a Rhabdovirus genome wherein the Rhabdovirus comprises a deletion of the nucleic acid sequence which encodes a G protein gene of the Rhabdovirus, and a nucleic acid which encodes a heterologous fusion polypeptide, and a nucleic acid which encodes a heterologous G stem polypeptide.

20. The recombinant Rhabdovirus of claim 19, wherein G stem polypeptide comprises a cytoplasmic tail domain, a transmembrane domain, and at least 23 amino acids of the carboxy terminus of the membrane proximal ectomain of a Rhabdovirus G protein.

21. The recombinant Rhabdovirus of claim 19, wherein the G stem polypeptide is a Rhabdovirus G stem polypeptide.

22. The recombinant Rhabdovirus of claim 19, wherein the G stem polypeptide comprises a cytoplasmic tail domain, a transmembrane domain, and a carboxy terminal membrane proximal ectomain of a Rhabdovirus G protein.

23. The recombinant Rhabdovirus of claim 22, wherein the G stem polypeptide comprises a polypeptide fragment of the G stem polypeptide.

24. The recombinant Rhabdovirus of claim 19, wherein the fusion protein is a F protein.

25. The recombinant Rhabdovirus of claim 19, wherein the fusion protein is from a paramyxovirus SV5.

26. The recombinant Rhabdovirus of claim 19, wherein the Rhabdovirus further comprises a nucleic acid encoding a heterologous antireceptor protein.

27. The recombinant Rhabdovirus of claim 26, wherein the antireceptor is a heterologous single chain Fv fragment.

28. The recombinant Rhabdovirus of claim 27, wherein the heterologous single chain Fv fragment is a prostate specific heterologous single chain Fv fragment.

* * * * *